(12) United States Patent
Trevino et al.

(10) Patent No.: US 7,020,844 B2
(45) Date of Patent: Mar. 28, 2006

(54) METHOD AND APPARATUS FOR MANAGING WORKFLOW IN PRESCRIBING AND PROCESSING MEDICAL IMAGES

(75) Inventors: Scott E. Trevino, Waukesha, WI (US); Ranjeeta Singh, Milwaukee, WI (US); Josef Debbins, Waukesha, WI (US); Paul Licato, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 522 days.

(21) Appl. No.: 09/683,129

(22) Filed: Nov. 21, 2001

(65) Prior Publication Data

US 2003/0095150 A1 May 22, 2003

(51) Int. Cl.
*G06F 17/00* (2006.01)
(52) U.S. Cl. ...................... 715/772; 715/764
(58) Field of Classification Search ................ 345/772, 345/778, 823, 824, 810; 715/772, 764
See application file for complete search history.

(56) References Cited

U.S. PATENT DOCUMENTS

| | | | | |
|---|---|---|---|---|
| 5,530,907 A | * | 6/1996 | Pavey et al. ................. 710/69 |
| 5,786,816 A | * | 7/1998 | Macrae et al. .............. 715/763 |
| 5,950,002 A | * | 9/1999 | Hoford et al. .............. 717/109 |
| 6,063,030 A | * | 5/2000 | Vara et al. ................... 600/437 |
| 6,426,759 B1 | * | 7/2002 | Ting et al. .................. 715/763 |
| 6,674,449 B1 | * | 1/2004 | Banks et al. ................ 715/740 |
| 6,687,527 B1 | * | 2/2004 | Wu et al. .................... 600/410 |

FOREIGN PATENT DOCUMENTS

WO    WO 02/39899 A2 *  5/2002

* cited by examiner

*Primary Examiner*—Richard Hjerpe
*Assistant Examiner*—Michelle K. Lay
(74) *Attorney, Agent, or Firm*—Ziolkowski Patent Solutions Group, SC; Michael A. Della Penna; Carl B. Horton

(57) ABSTRACT

The present invention is directed to a method and apparatus that streamlines the process of prescribing and acquiring medical imaging experiments and data processing applications. The present application provides a modular intuitive and guided workflow having a graphical user interface that may be tailored and made singular and unique for each individual application. The user interface implements a guided management tool that incorporates the general principle that user activity is more efficient when it begins in the upper left-hand portion of the screen and proceeds horizontally across the screen moving from left-to-right and top-to-bottom. The user interface incorporates a number of tabs wherein each tab corresponds to a major prescription step. The tabs are aligned vertically along the left side of the user interface and are used to modularize the application workflow.

23 Claims, 20 Drawing Sheets

FIG. 20

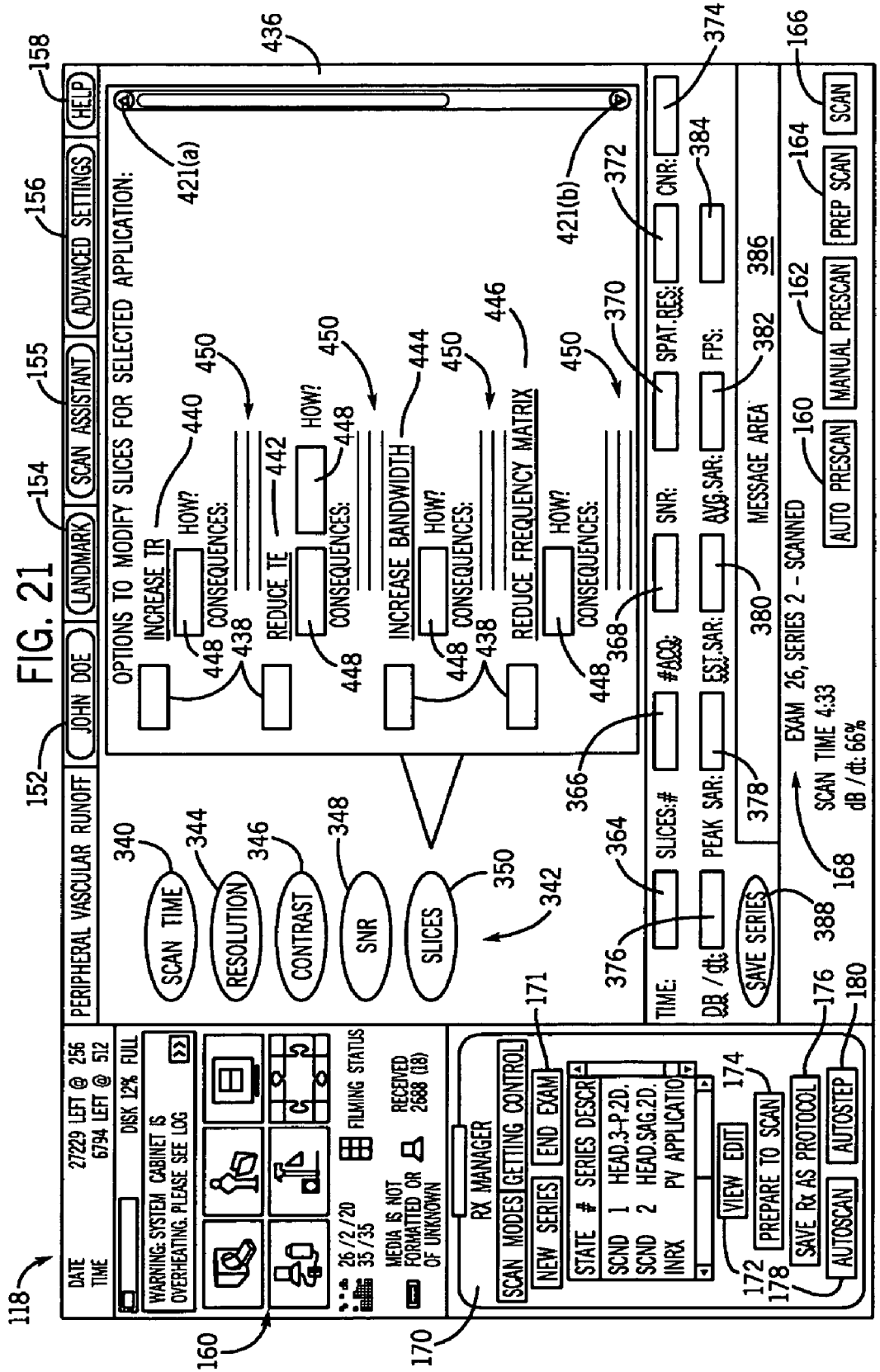

METHOD AND APPARATUS FOR MANAGING WORKFLOW IN PRESCRIBING AND PROCESSING MEDICAL IMAGES

BACKGROUND OF INVENTION

The present invention relates generally to medical imaging data acquisition and graphical user interfaces and, more particularly, to a method and apparatus for managing the prescription workflow of a medical imaging session and acquiring medical images in accordance with this managed workflow.

The present invention is directed to the management of workflow for the prescription, acquisition and post processing of medical imaging sessions. The invention is particularly useful in prescribing MR image acquisition. While known MR systems somewhat guide a user or MR technologist through the imaging session, there is a need for a workflow management tool that is more logical and intuitive than these known systems. Prescribing MR imaging sessions and/or experiments involves setting parameters that are used by the pulse sequence, in reconstruction, and the visualization systems to acquire MR imaging data. The number of parameters is often extensive and with these known systems there is insufficient logic, layout, and management to guide the user from one parameter to the next. These workflow tools are often singular, parameter intensive, not intuitive, complex, and not configurable.

Known workflow tools can take the form of a graphical user interface (GUI) that appears on the operating console of the MR system. These GUIs typically provide all the scan parameters to the user simultaneously, but with only a limited number of application-specific parameters. These parameters are grouped into logical clusters and presented to the user. However, the clusters of scan parameters are presented on the GUI in such a manner that does not generally support generalized, logical workflow. Further, these known systems often fail to provide a mechanism to logically guide the user from one set of parameters to the other. These systems tend to support workflow where the user input actions occur randomly over the screen instead of following a sequential, logical approach. In addition, since all of the scan parameters are presented to the user in a single window, the window often appears complex and congested which contributes to user confusion and potential input errors. These known workflow systems are commendable across the entire spectrum of MR applications however, there is a need for a GUI that is tailored to a particular clinical or research application. That is, there is a need for a GUI that reflects the MR application currently running.

Typically, the workflow for these MR systems is restricted to presenting all scan parameters and associated application features on a single GUI presentation. As a result, the GUI does not efficiently guide the user through application prescription or acquisition, does not provide application information, lacks modularity, is not configurable, and introduces unnecessary complexity for prescribing MR experiments and acquiring MR images.

Therefore, it would be desirable to design a method and apparatus for managing the workflow for prescribing MR imaging sessions and experiments that would be adaptable to a particular MR application and be intuitive and logical in the presentation of prescription parameters.

BRIEF DESCRIPTION OF THE INVENTION

The present invention is directed to a method and apparatus that streamlines the process of prescribing and acquiring MR experiments and MR data processing applications. The present application further provides a modular intuitive and guided workflow having a graphical user interface (GUI) that may be tailored and made singular and unique for each individual application. The GUI recognizes the general principle that user activity begins in the upper left-hand portion of the screen and proceeds horizontally across the screen moving from left to right and top to bottom. The GUI incorporates a number of tabs wherein each tab corresponds to a major prescription or image post-processing step. The tabs are aligned vertically along the left side of the screen, although they may optionally be aligned horizontally across the top of the screen, and are used to modularize the application workflow. These tabs lead the user through the steps necessary to prescribe the application as well as give the user valuable information regarding the purpose of each step via a tab label. Status indicators corresponding to each tab are also provided to convey the state of the activities associated with each tab, whether or not the tab has been selected, or if the associated task was completed successfully or not. The GUI also makes available user messages, scan information, and a list of the components necessary for the user to quickly initiate scan activity. The GUI also conveys the state of the current application and allows for the user to determine if the current application is able to scan, if another application is currently scanning, scan times, as well as other important scan information.

Therefore, in accordance with one aspect of the present invention, a GUI is provided for prescribing medical imaging sessions, acquiring medical images, and processing imaging data. The GUI comprises a plurality of modularizing selectors configured to facilitate workflow through a medical imaging application. A plurality of status indicators are also provided wherein each status indicator corresponds with a modularizing selector and configured to display at least one of selection of the modularizing selector and completion of tasks associated with the modularizing selector. The GUI further includes a messaging module configured to automatically display messages regarding the medical imaging application.

In accordance with another aspect of the present invention, a graphical workflow management tool is provided for prescribing an imaging scan. The tool includes a GUI configured to be visually displayed on a console of a medical imaging system. The tool further includes a plurality of prescription tabs aligned vertically on the GUI. A plurality of status indicators are also provided on the GUI wherein each indicator is configured to display a status of activities for a corresponding prescription step. The tool further includes a plurality of tabs aligned horizontally on the GUI that upon selection display a context-specific user interface.

In yet another aspect of the present invention, an apparatus includes a computer programmed to receive a launch application command and launch the application in response thereto. The computer is further programmed to receive a number of application steps identifier. The computer is further programmed to display a GUI on a console the GUI having a number of tabs equal to the number of identified application steps. Each tab corresponds to an interaction performed by a user, such as prescription, scanning, etc. The computer is also programmed to display the status of application steps. The computer is also programmed to receive another prescription command and acquire images in response to the received another application step.

In a further aspect of the present invention, a method of acquiring images is provided and includes receiving a launch application instruction and launching the application. The method further includes determining a number of prescription steps based on a received user input. The method also includes displaying a GUI for prescribing an imaging session. The GUI is configured to include a number of modularizing tabs wherein each modularizing tab represents a prescription step.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 20 is a representation of a graphical user interface for modifying the signal to noise ratio for the representative medical imaging application in accordance with the present invention.

FIG. 21 is a representation of a graphical user interface for modifying slice information for the representative medical imaging application in accordance with the present invention.

DETAILED DESCRIPTION

Figure 1:
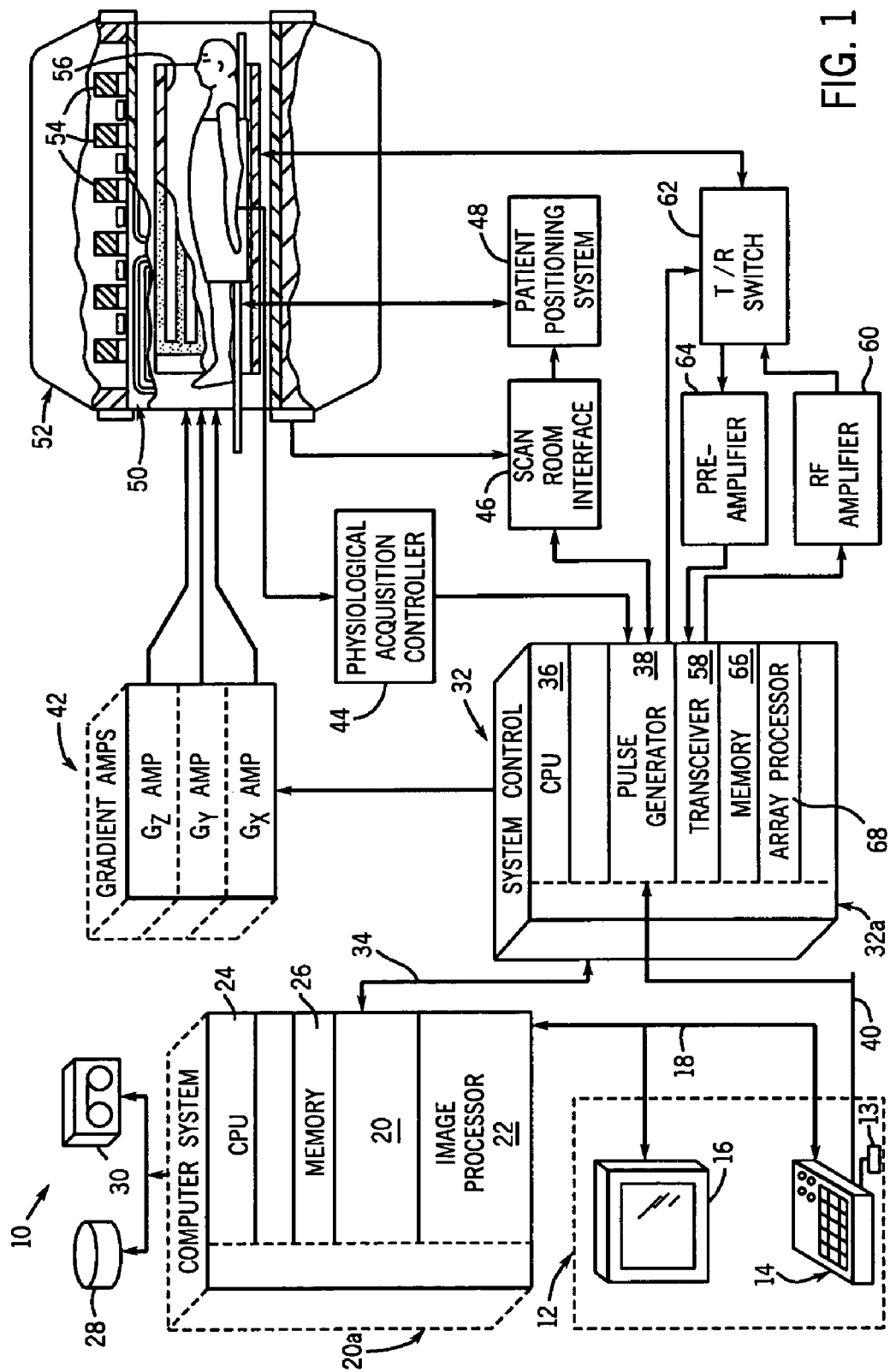
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention is directed to a method and apparatus of directing workflow for medical imaging experiments and sessions. The invention utilizes an hierarchical scheme to facilitate improved workflow. The workflow tool will be described with respect to a Peripheral Vascular (PV) application using MR imaging technology which is considered the "super" application because it is defined by the combination of multiple sub-applications. The teachings of this invention are not limited, however, to a PV application or MR technology. The PV application of the present invention varies from a traditional application of known MR systems. Specifically, the PV application is a combination of a 2D gradient echo application and a 3DSPGR (Three-Dimensional with Spoiled Gradient Echo Pulse Sequence) application. Therefore, the PV application GUI is a composition of the components that it defines as well as the components from other "sub" applications. The present invention includes a GU 100 designed to dynamically adjust the layout and distribution of screen space throughout the scan. The PV application GUI can generally be thought of as a collector. As a result, nothing prohibits the "sub" applications from similarly acting as a recursive collection of any number of other application GUIs.

The present invention improves workflow by increasing the intuitiveness of the application workflow, making the application more flexible, improving usability, decreasing the number of user interactions/steps, and incorporating fault tolerance. In one preferred embodiment, the PV application may be launched by "double clicking" an icon displayed on the console 16, FIG. 1. By launching the PV application, the user may create a new exam, edit an existing protocol, and/or enter patient information.

Figure 2:
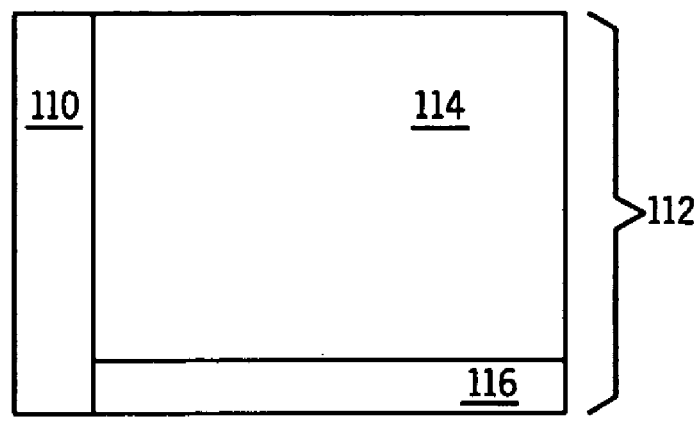
FIG. 2 is a representation of a graphical user interface illustrating the allocation of screen space in accordance with the present invention.

FIG. 2 is an illustration of a layout of a GUI in accordance with the present invention. GUI 100 is designed to dynamically adjust the layout and distribution of screen space throughout the scan. As illustrated, GUI 100 includes a generic control region 110 which occupies approximately 20% of the available screen space, whereas the remaining 80% of the screen space is reserved for control of a local or particular application 112. In this embodiment, the region 110 will retain 20% of the total screen space and thereby limit the space available for region 112. In this embodiment region 112 includes prescription area 114 and an operations area 116.

Figure 3:
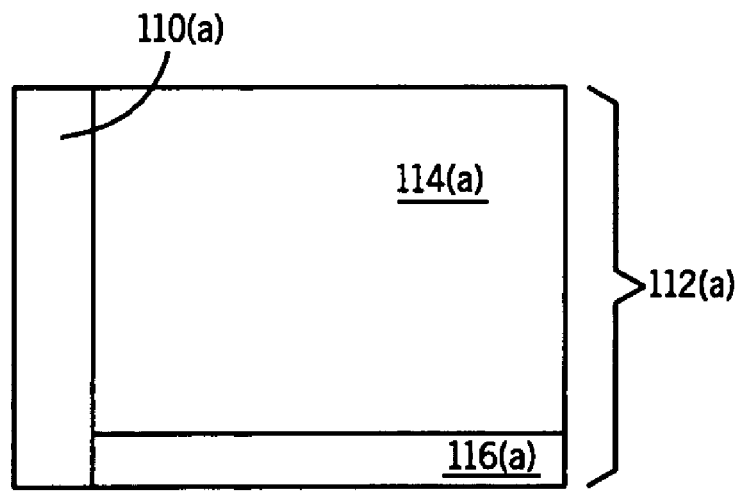
FIG. 3 is a representation of graphical user interface similar to that shown in FIG. 2 illustrating allocation of screen space in an alternate embodiment of the present invention.

However, in another embodiment as shown in FIG. 3, GUI 100(*a*) includes space 112(*a*) which is distributed to include region 114(*a*) but region 116(*a*) is reserved for generic control operation. This occurs when the generic control application has the scanner resources and the control for the prescription application is simply being used to prescribe a scan session. In this embodiment, space associated with the Lx application 110(*a*) and 116(*a*) retains an additional 10 15% of the screen space. Therefore, the local application may utilize only 65 70% of the total screen space for conveying information.

FIGS. 2 and 3 illustrate various embodiments for allocating finite screen space among several medical imaging applications. Distributing the screen space in a position similar to that shown in FIGS. 2 and 3 facilitates ease of user interactions between applications. It should be noted that the present allocations described above are for illustrative purposes and are not intended to limit the scope of the invention.

Figure 4:
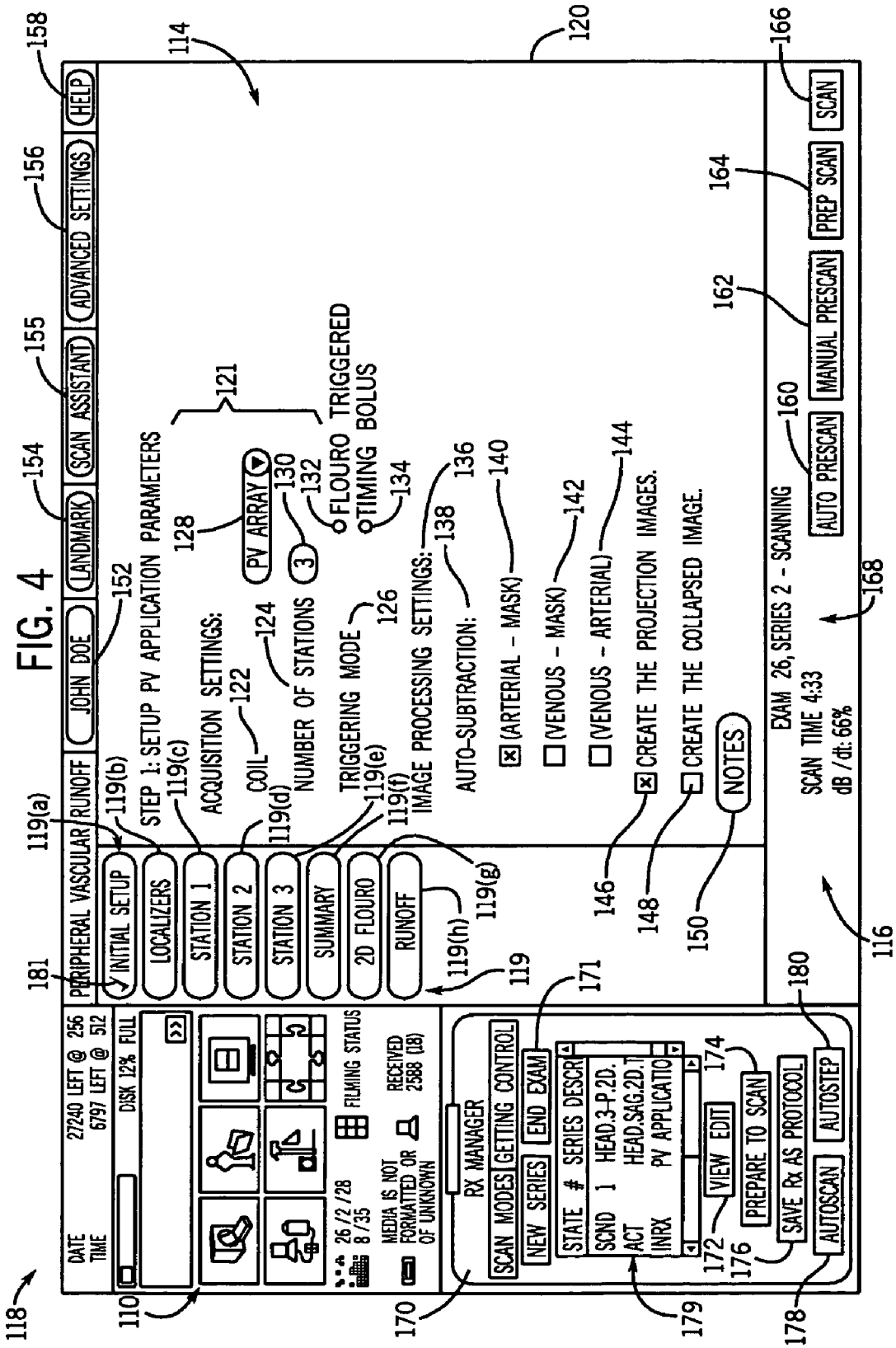
FIG. 4 is a representation of a graphical user interface for setting up initial scan application parameters for one representative medical imaging application in accordance with the present invention.

Referring now to FIG. 4, GUI 118 is shown having an initial setup window. GUI 118 is displayed when the PV application is first launched or, alternatively, when the user selects "Initial Setup" tab 119(*a*) of modularizing tab array 119. This view presents the user with an "Initial Setup" window 120. Window 120 allows the user to perform the initial setup for the PV application. The user may establish settings such as acquisition settings 121. Included in the acquisition settings 121 are coil 122, number of stations 124, and triggering mode 126. Corresponding to coil 122 is a drop-down menu 128 that allows a user to select a coil such as a PV array. The user may input the number of stations in field box 130 and select the triggering mode 126 by choosing fluro triggered radial button 132 or timing bolus radial button 134. If the user inputs a number stations greater than three, GUI 118 automatically updates to add additional modularizing tabs to array 119.

Array 119 not only includes "Modularizing" tab 119(*a*) corresponding to initial setup, but also includes a "Localizers" tab 119(*b*), a "Station One" tab 119(*c*), a "Station Two" tab 119(*d*), a "Station Three" tab 119(*e*), a "Summary" tab 119(*f*), a "2D Fluro" tab 119(*g*), and a "RunOff" tab 119(*h*). Modularizing tab array 119 is vertically arranged along a left side of window 120. The tabs 119(*a*)–(*h*) correspond to each prescription step of an medical imaging scan session. The nomenclature provided for each tab is for illustrative purposes as differing medical imaging applications would utilize different tab names. The tabs are arranged vertically and, in a preferred embodiment, in order of execution. That is, tabs 119(a)–(h) are logically arranged to guide a user through prescription of the medical imaging scanning session. When a particular tab is selected by a user, the tab is highlighted in a known manner to indicate selection of the particular tab. As shown in FIG. 4, the appearance of GUI 118 is representative of that which appears upon user selection of "Initial Setup" tab 119(a).

GUI 118 further facilitates user selection of image processing settings 136 such as identifying the proper auto subtraction processing 138. In a preferred embodiment, the user may select one of arterial-mask 140, venous-mask 142, or venous-arterial 144. The user may also indicate whether to create projection images by selecting check box 146 or create a collapsed image by selecting check box 148. GUI 118 further includes a "Notes" button 150 that once selected by a user will cause a GUI or window to appear for entering of notes related to the instant medical imaging scanning session or protocol. A "Patient" button 152 is also provided that upon activation by a user will display information relating to the patient. A "Landmark" button 154 as well as an "Advanced Settings" button 156 are also provided and will be discussed shortly. Selection of "Landmark" button 154 causes another window (not shown) to appear which is configured to facilitate proper positioning of the scan subject. If the user has any questions or needs assistance relating to the prescription steps, the user may select "Help" button 158 to display various topics to assist the user with prescribing the imaging scan. "Scan Assistant" button 155 will be discussed with reference to FIGS. 17–21.

As indicated previously, GUI 118 includes a prescription region 114 and generic control regions 110, 116. Region 116 includes an "Auto Pre-Scan" tab 160, a "Manual Pre-Scan" tab 162, a "Prep Scan" tab 164, and a "Scan" tab 166. User selection of these tabs 160–166 varies depending upon the particular application. Region 116 also includes status identifiers 168 that display the current scan time, completion status, and activation status.

Region 110 includes an Rx manager interface 170 that displays various information regarding the particular prescription. The Rx manager 170 includes a "View/Edit" tab 172, a "Prepare To Scan" tab 174, a "Save Rx As Protocol" tab 176, an "Auto Scan" tab 178, and an "Auto Step" tab 180. Tabs 172–180 will display upon user selection thereof a corresponding window to facilitate user completion of the selected task or activity. A number of additionally status indicators and tabs are also provided in region 110 to provide information to the user as to the status of the scan session.

In a preferred embodiment, the user will make changes to the PV application settings when defining a new protocol. That is, a user may make selections in window 120 of GUI 118 and throughout other portions of the application, such as an "Advanced Settings" window (to be discussed shortly), and then save the settings as a new protocol. As a result, all subsequent executions of this PV application could utilize the created protocol and the user would typically only review the settings in the "Initial Setup" page and then click the next tab, the "Localizers" tab 119(b), to begin the acquisition of data. When the user has entered all of the data for a particular tab, a check 181 will appear as a label to indicate that the necessary steps have been achieved.

Still referring to FIG. 4, there are three stations for this application as indicated in the "Number of Stations" text field 130. This is important because the number of stations determines the number of corresponding steps/tabs 119 for this application. Specifically, there is one tab per station for the acquisition of the 3D volume mask images and there is one localizer image set acquired per station. For example, if there were only two stations defined there would be one fewer tab (i.e. "Station 3" tab 119(e) would not be necessary), only two localizers listed under the "Localizers" tab 119(b), and only two stations for arterial and venous images. If the user entered six stations on the "Initial Setup" page 118, the number of tabs 119 would update to add three more (i.e. "Station 4", Station 5", and "Station 6"), there would be six localizers under the "Localizers" tab 119(b), and six stations for arterial and venous images.

The "Arterial-Mask" option 140 specifies that after acquisition of the arterial run images a set of subtracted images should be automatically generated using the masks. It should be noted that the auto-subtraction option 138 should be an improvement over existing systems as it automates and simplifies this application.

Workflow within this application works in the following way. A user navigates an application through a series of steps as conveyed by the tabs 119 on the left side of the screen 114. There is a one-to-one relationship between the number of tabs 119 and the number of steps in the PV application. Therefore, in this embodiment, the PV application has eight steps corresponding to the number of tabs 119. Preferably, the user moves through these tabs 119 from top to bottom. This is expected to be the preferred manner of completing this application, however, the user may complete the steps in any order. As all the tasks with each tab 119 are completed (i.e. the "Localizer" tab 119(b) is only considered complete when the task of acquiring the localizers is completed) each tab 119 displays a checkmark icon 181. This icon will indicate to the user that the step has been successfully completed. If a step has not been completed, partially or not at all, the tab will not have a check. Also, all seven steps prior to the "RunOff" step (i.e. the last step) must have been successfully completed in order to acquire the arterial and venous runs. That is, the PV application requires that all steps prior to the final step of arterial and venous acquisition be performed. The user will be notified of this requirement, if they try to acquire the "runs" without completing all prior steps, via the "Scan" button 166 being disabled and a message being displayed in the "Application Message" area 116.

Figure 5:
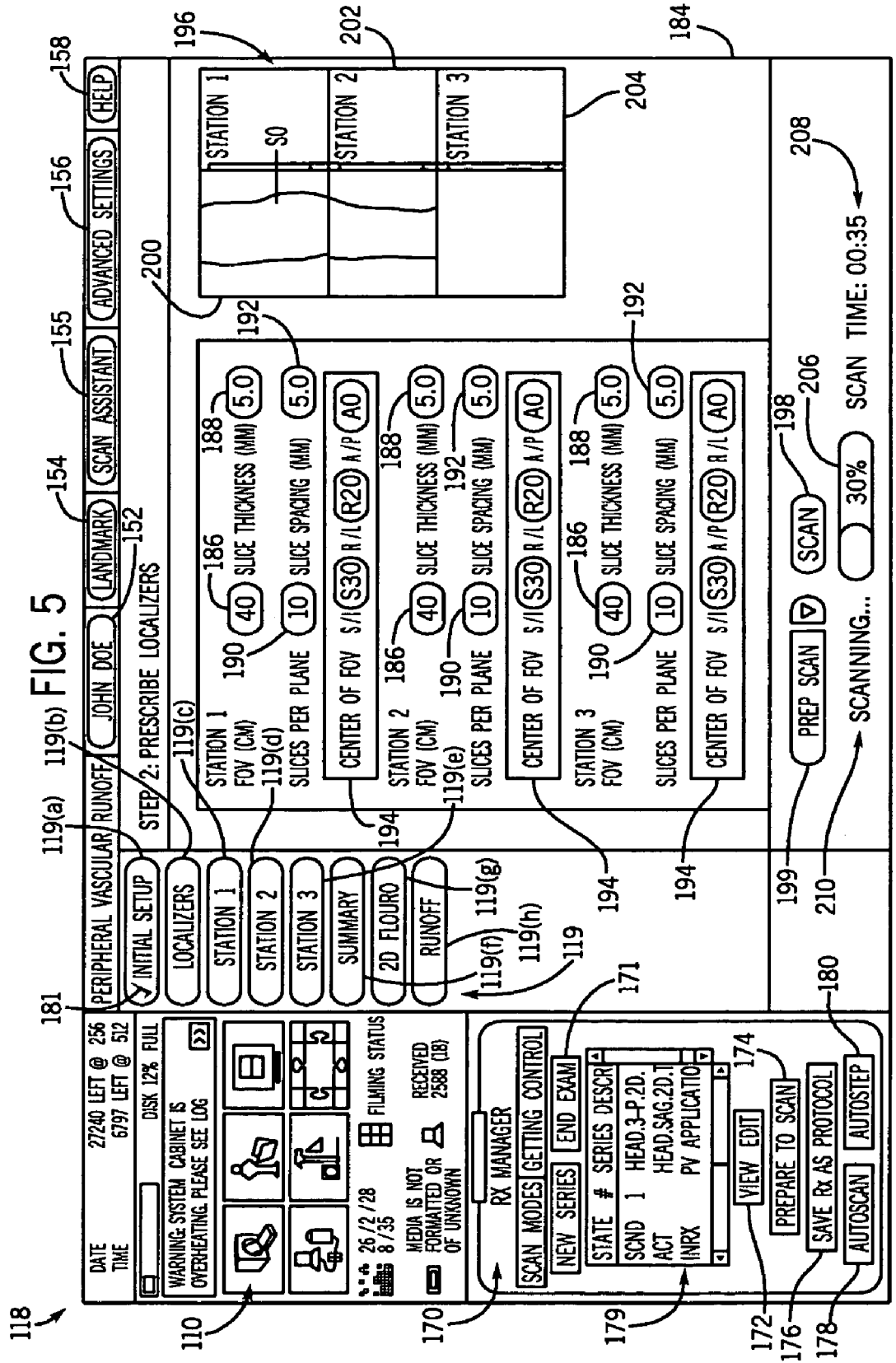
FIG. 5 is a representation of a graphical user interface similar to that shown in FIG. 4 for prescribing localizers for the representative medical imaging application in accordance with the present invention.

Referring now to FIG. 5, a representation of GUI 118 upon user selection of "Localizers" tab 119(b) is shown. Window 184 appears within GUI 118 and allows the user to review and/or change the scan parameters for each of the station localizers (as defined in the "Initial Setup" mentioned earlier). FIG. 5 is an illustration of how the user may multi-task effectively by "prescribing ahead" a local application while the system is busy scanning another generic series. The user may view "Patient Information" by clicking button 152 at the top of the screen in the "Global Information Access" area that contains the name and ID of the patient. A pop-up dialog will then be displayed on top of the PV application GUI 118 similar to that shown in FIG. 6 (which will be described below).

Window 184 allows the user to review and/or change the scan parameters for each station. The user may adjust the FOV 186, slice thickness 188, slices per frame 190, and slice spacing 192 for each station. The user may also review and/or edit scan parameters relating to the center of the FOV 194.

Once the user inspects and verifies the scan parameters presented, the user may select "Prepare to Scan" button 198 to initiate a resource switch to transfer the scanning resources and download. The user can then select "Scan" to initiate a scan for the localizer application and perform any necessary Prescan operations and then scan the localizers.

The resource switch is a very important difference between the present system and other known systems. In the present invention, one must consider the consequences of the first selection of a scanning operation. This will cause a scanning resource switch, whether it is the first selection of a scan operation in the localizer application when the scanner is "owned" by the global application, or vice versa. Therefore, when a user selects scan, the first thing that occurs is a resource switch.

A "Humanoid" 196 is displayed in a right portion of window 184. When the "Scan" button 198 is selected, all three localizers are automatically scanned and images are displayed in the "Humanoid". This is an important step in improving the user workflow by automating redundant steps and streamlining how the user moves through this system. In a preferred embodiment, one cannot scan localizers in any other fashion. If there are more or less stations defined, as part of the initial setup, then there will be fewer or more localizers to be acquired. In either case, the localizer acquisition will be done automatically.

After selecting "Scan" button 198, the GUI 118 will set forth the progress being made towards completion of the resource switch and scan in one of three ways.

First, the "Humanoid" 196 displayed to the immediate right of the localizer scan parameters window 184 will display localizers from each station as they are being acquired. That is, when the first localizer image from the first station (most superior in this case) is acquired the middle sagittal image 200 will be displayed in the top viewer of the "Humanoid" 196. Each subsequent image 202, 204 acquired for that station is also displayed. The "Humanoid" 196 provides the capability for the user to scroll through the images 200–204. However, in one embodiment, the images displayed will only be sagittal images. As the system finishes acquiring the localizer from one station and then begins acquisition of a localizer at another station, the "Humanoid" 196 updates as necessary until the scanning completes.

The second way in which the user is made aware that the global application system is scanning is via progress bars 206 and a timer 208, both of which indicate the progress towards the completion of the resource switch and localizer acquisition. Another bar (not shown) shows progress towards the completion of the resource switch on the scanner. Bar 206 indicates the percentage of the task completed based on images acquired versus total images. The "resource switch" progress bar will be displayed first and will be replaced by the "image acquisition" progress bar immediately after it completes. Timer 208 shows the count down of time for the image acquisitions. Timer 208 will be displayed when the "Scan" button 196 is selected, but will not begin counting down until the scanner actually begins the scan.

The final way in which the user is made aware that the global application system is scanning is via the desktop icon displaying the word "Scanning" 210, the scan operation buttons being disabled, and, in most experiments, the user can hear the scanner as it is scanning.

Figure 6:
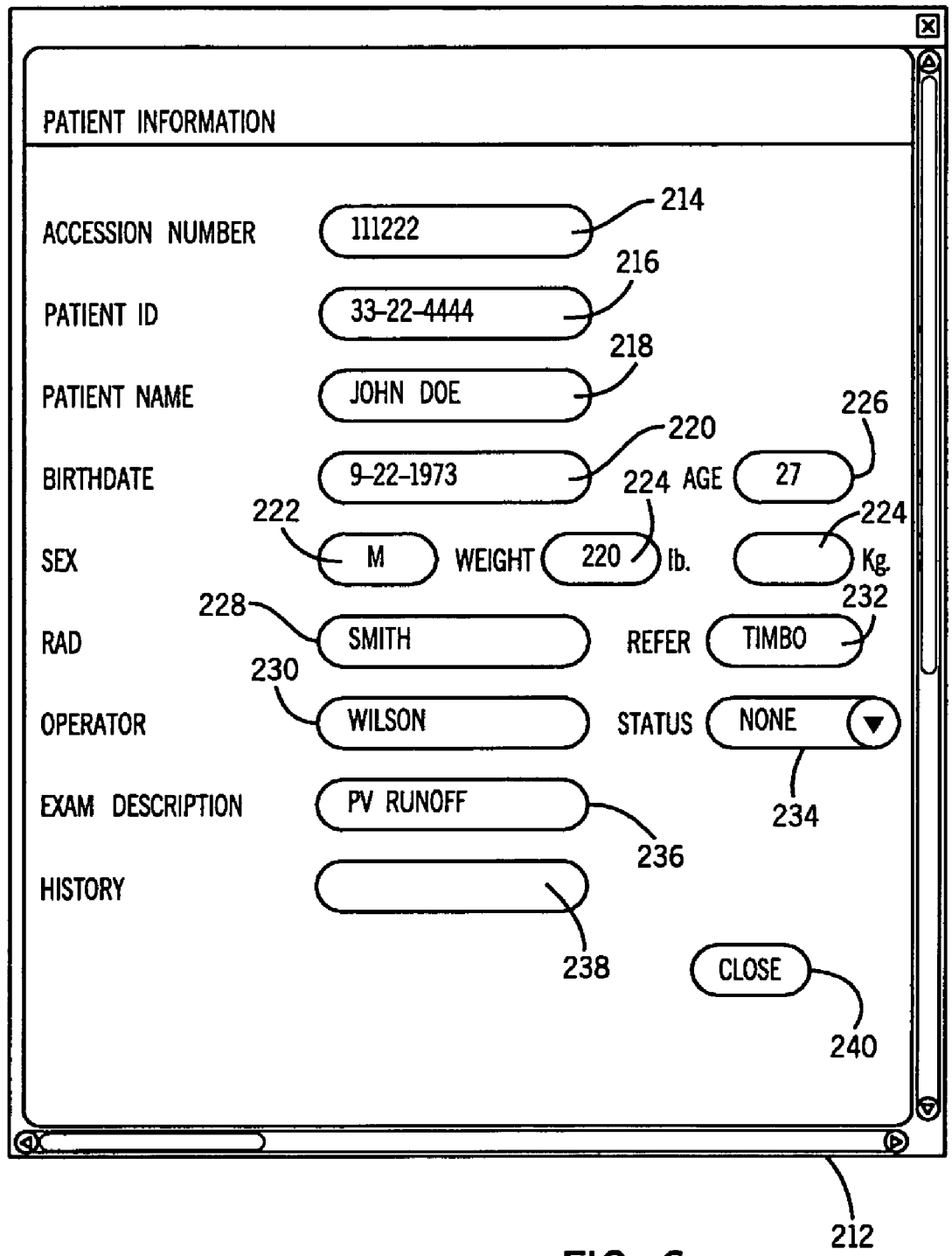
FIG. 6 is a representation of a graphical user interface for the inputting of patient information in accordance with the present invention.

Referring now to FIG. 6, "Patient Information" window 212 appears upon user selection of patient tab 152, FIG. 4. Window 212 allows the user to view an accession number 214, a patient ID 216, name 218, birth date 220, sex 222, weight 224, age 226, radiologist 228, operator 230, reference 232, status 234, exam description 236, and history 238. A "close" button 240 is also provided to allow the user to close window 212.

Figure 7:
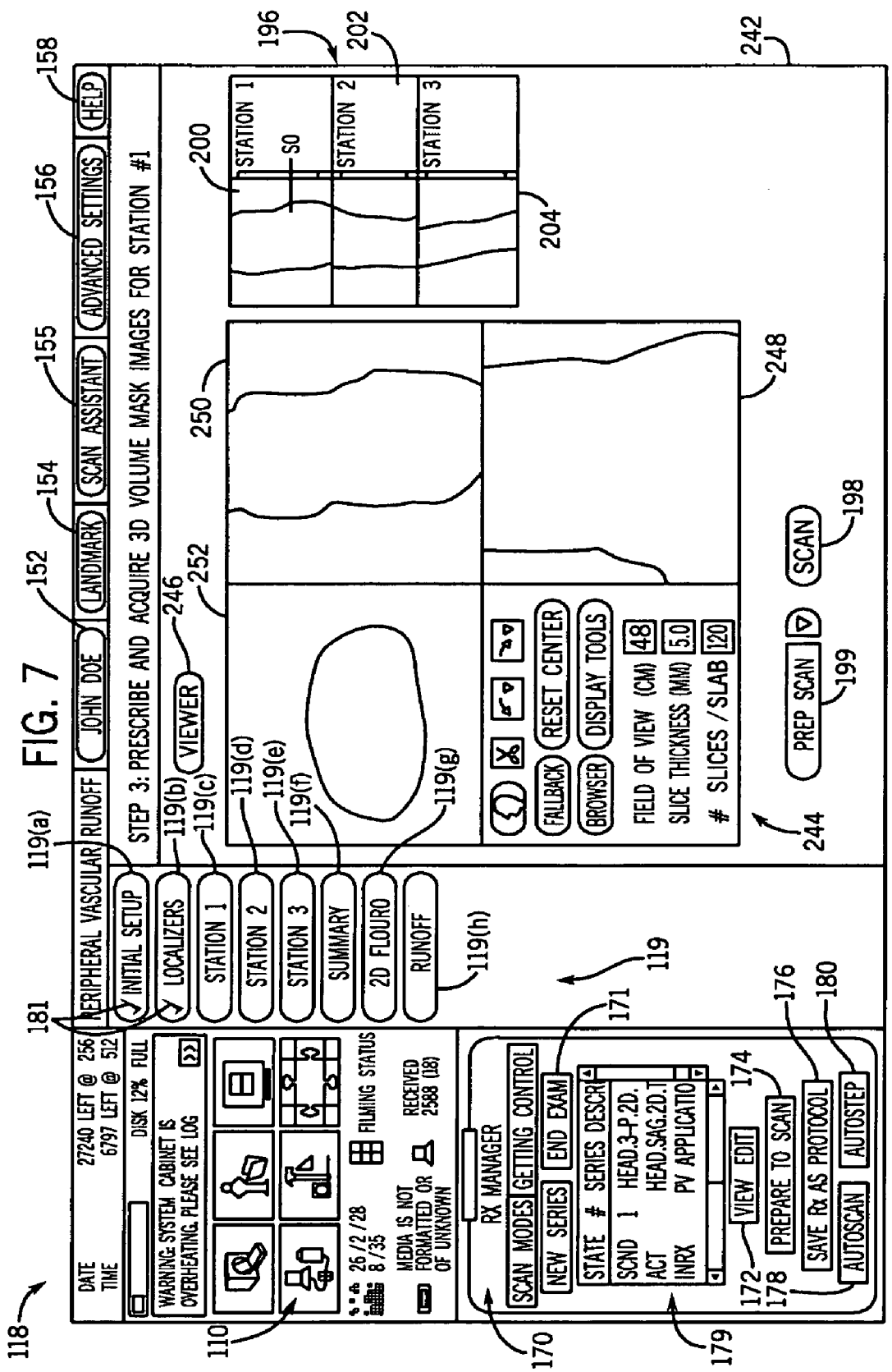
FIG. 7 is a representation of a graphical user interface for prescribing and acquiring images in accordance with the present invention.

Referring to FIG. 7, once the user has acquired the localizers for the three specified stations, the user may select the next step, "Station 1" tab 119(c), in order to display window 242 to prescribe and acquire the 3D mask images for the first station. The user may also proceed to the next step before acquisition of images. In this embodiment, the user cannot perform any further interactions associated with this step as the required localizer images have not been acquired. Alternatively, the user may select scan and move to the next step while the image acquisitions are occurring. In this embodiment, the user can begin the next step once the first localizer is acquired. Window 242 contains the same "Humanoid" 196 in the same location as in FIG. 5. However, instead of the localizer imaging parameters for each localizer being presented, there is a 3-pane GRx tool 244. Directly above the GRx tool 244 is a toggle button 246 that allows the user to move between viewing the acquired 3D mask images 248–252 and interacting with the 3-plane GRx tool 244. Below the GRx tool 244 is the "Prep Scan" combination button 199 and the "Scan" button 198 as shown in FIG. 5. These two buttons will not become active until after the user places the prescription on the image and no other application is scanning.

Once the 3D volume has been placed on the localizer images the user may interact with the 3D volume by dragging and rotating the 3D volume. Also, the user may use the tools located in GRx 244.

Figure 8:
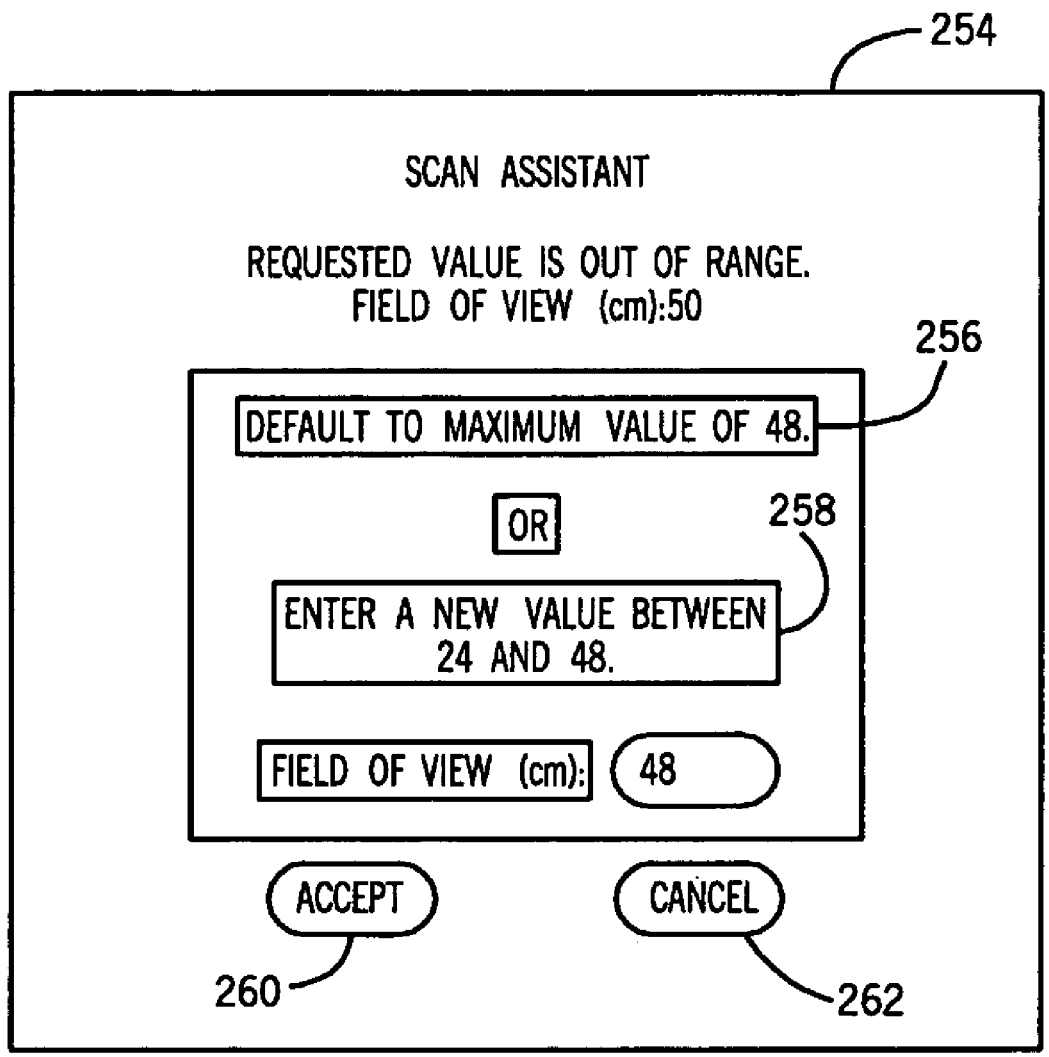
FIG. 8 is a representation of a pop-up dialog for use with the present invention.

Referring to FIG. 8, most medical imaging applications employ policies for its scan and application parameters that prevent the user from entering invalid prescriptions. One tool that enforces these policies is referred to as "Scan Assistant" window 254. In the PV application, the policy will be to "popup" a dialog 254 whenever a user enters parameters that are invalid. This dialog 254 will indicate to the user the error and force selection of another valid value. The user may choose between a default value 256 the system chooses, which is the next closest value to the invalid entry, or may enter another valid value 258. This tool 254 will prevent the medical imaging application from being in an invalid state. User may accept the changes by selecting "accept" tab 260 or cancel the change by selecting tab 262. An alternate "Scan Assistant" tool will be described with respect to FIGS. 17–21.

Figure 9:
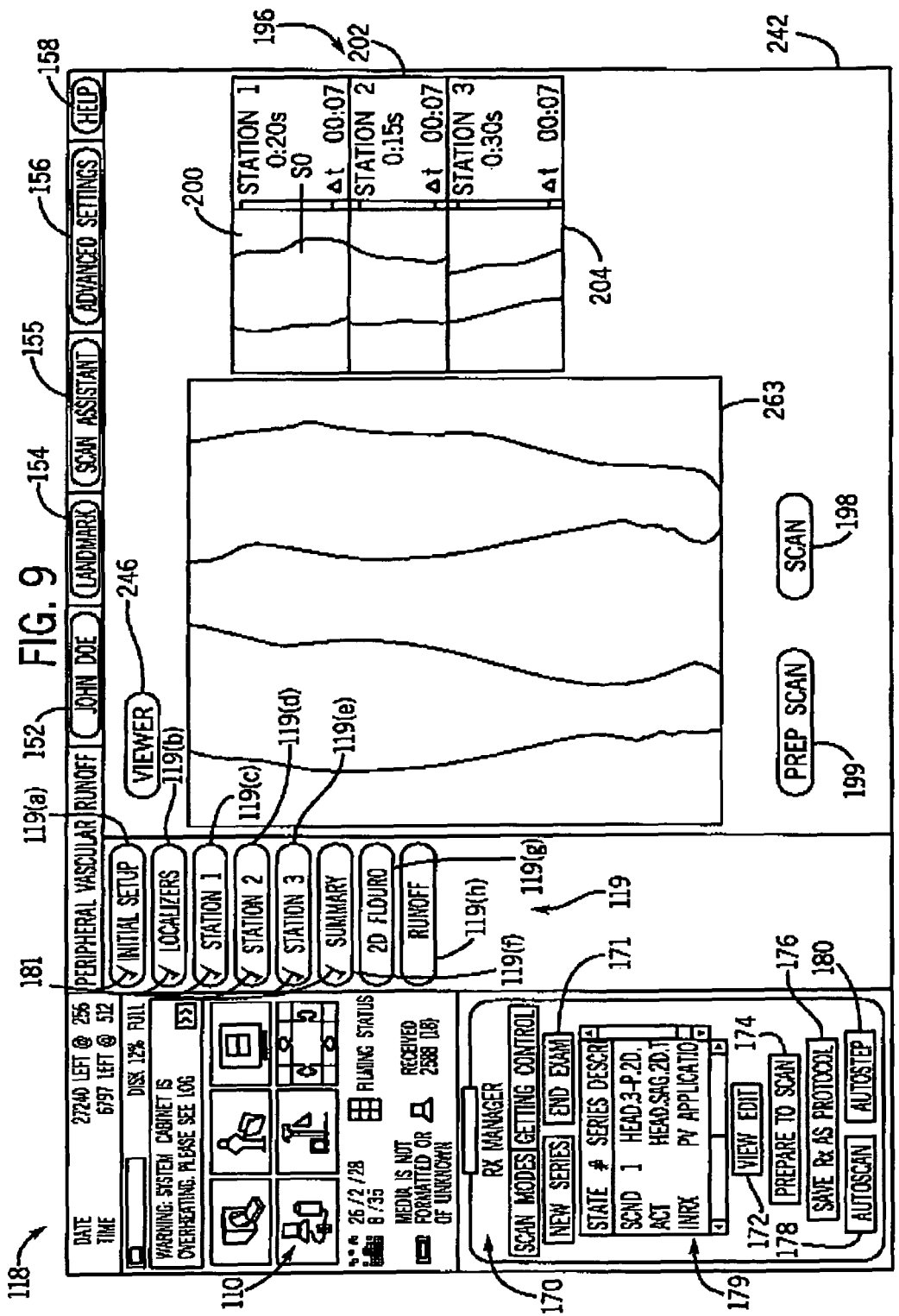
FIG. 9 is a representation of a graphical user interface for displaying images of a scan station.

Referring again to FIG. 7, to acquire the 3D mask images for this station, the user would select "Scan" button 198. As described earlier, the "image acquisition" progress bar 206 and timer 208 are displayed while acquiring the images. Also, once the "Scan" button 198 is selected, the area of the screen occupied by the GRx tool 244 is replaced with an image viewer, FIG. 9. Referring now to FIG. 9, the image viewer 263 associated with "Station 1" button 119(c) is displayed can be used to scroll through the acquired images as well as performing basic image operations such as window level and pan/zoom. In addition, the "Humanoid" 196 displays the 3D volume that was prescribed on the associated localizer and a "GRx/Viewer" toggle button 246 becomes active.

The "Humanoid" 196 also enables the viewer to display the localizer images selected to gain focus and also allows for the images in these viewers to be scrolled, pan/zoomed, and window leveled. The "Humanoid" 196 enables viewers to be selected which causes the PV application to switch to the associated prescription. For example, if the user "double-clicks" the third viewer in the "Humanoid" (i.e. station 3), the window associated with "Station 3" tab 199(e) will become selected and the user can move forward with this step. Further, "Humanoid" 196 displays information such as the iso-center, station number, station acquisition time, and the time for table motion. Because there are three stations defined there are three 3D masks to be prescribed and acquired.

Figure 10:
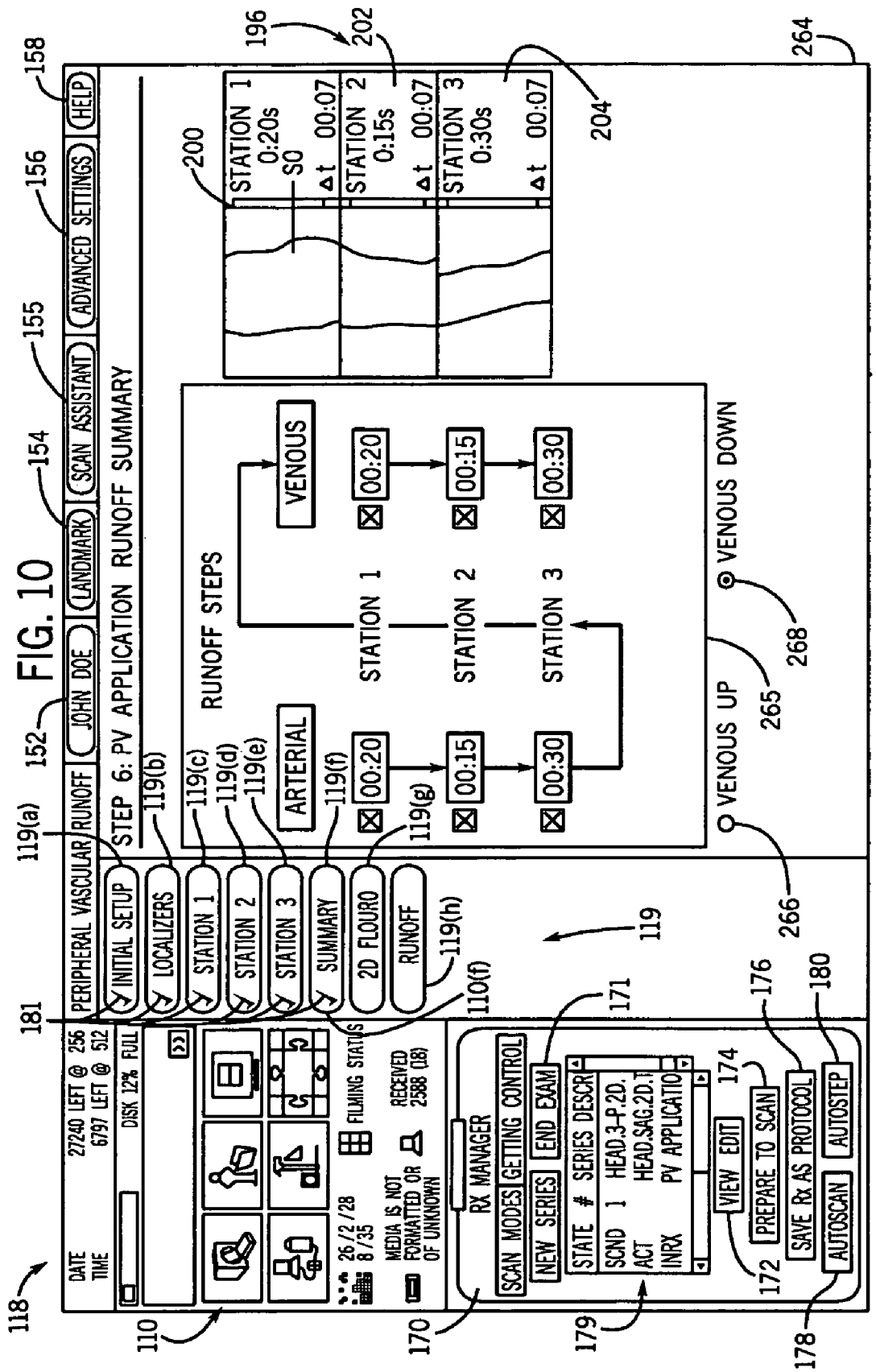
FIG. 10 is a representation of a graphical user interface for displaying summary data for the representative medical imaging application in accordance with the present invention.

Referring now to FIG. 10, after all mask image sets for each station have been acquired, the user may proceed to the "Summary" tab 119(f). The purpose of "Summary" window 264 is to present the user with the option of reviewing the acquisition order, time to acquire the arterial and venous images, and to "skip" acquisition of any arterial or venous phase or to change number of phases. All of this is accomplished via the information panel 265 displayed to the left of the "Humanoid" 196.

Window 264 clearly illustrates to the user everything that is scheduled to occur during the acquisition of the arterial and venous images. Things illustrated include:

Two columns indicating the arterial and venous acquisitions through the use of colored labels (i.e. red for arterial, blue for venous).

Colored labels contain the scan time for each series.

Check boxes next to the boxes allow the user to select or skip the acquisition. Therefore, in order to skip any step, the user only has to uncheck the check box associated with the particular acquisition.

Panel clearly shows the start of the acquisition as well as the total time listed for the acquisition. This number will dynamically update based on order selected and what is and is not being acquired.

In addition to the panel 265, there are also two buttons 266, 268 that the user can choose from in order to define the order of arterial and venous acquisition. One selection, "Venous Up" 266 acquires the arterial images superior to inferior and then the venous images inferior to superior thus reducing table movement. The second option is "Venous Down" 268 which acquires both the arterial and venous images superior to inferior. In one embodiment, "Venous Down" 268 is selected by default.

In addition to all that can take place during the "Summary" step, the present invention allows the user to re-acquire the 3D mask images for a particular station. Since the user may change the prescription for the 3D masks for station two and then re-acquire the images, the user need follow the same steps mentioned above when they first prescribed and acquired the 3D masks for station two. That is, "Station 2" tab 119(d) is selected and the GRx tool is used to fix the prescription. The user then presses the "Scan" button. Reacquisition of mask images for station 2 does not affect the previously acquired data for the other stations. Once this is completed, the user selects the "Summary" tab once again to again review a summary of the data acquisition.

Figure 11:
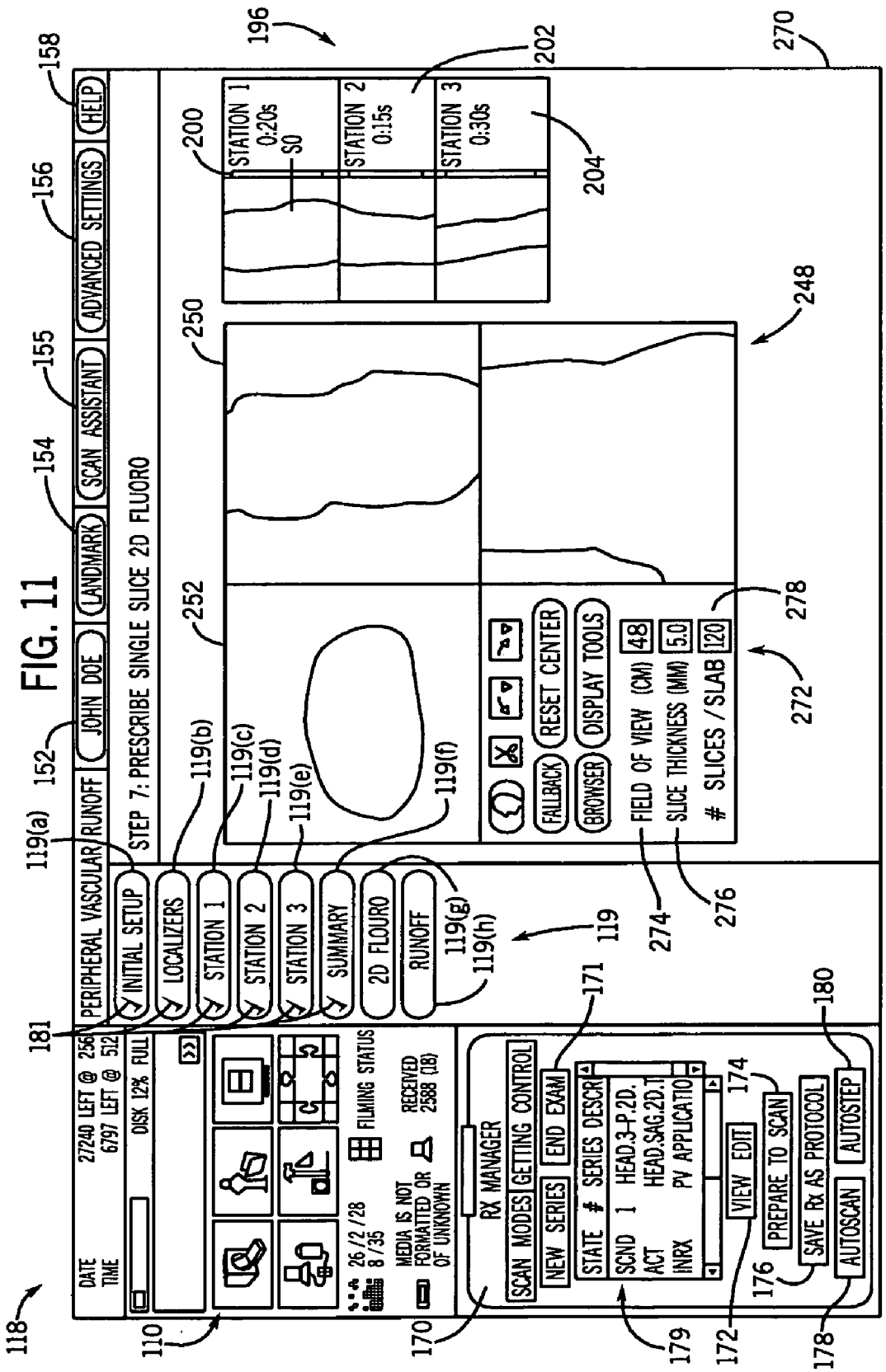
FIG. 11 is a representation of a graphical user interface for prescribing a particular medical imaging application in accordance with the present invention.

Referring to FIG. 11, the present invention allows for prescribing of a fluoroscopy by selecting modularizing tab 119(g) from GUI 118. Upon selection of tab 119(g), window 270 is displayed. Window 270 includes a GRx tool 272 for 2D prescription that enables the user to input various fluoroscopy parameters such as FOV 274, slice thickness 276, and number of slices per slab 278. "Humanoid" 196 remains displayed in a right portion of the screen as well as localizer images 248–252.

After prescribing the Fluoro acquisition, the user may then select "Runoff" tab 119 (h) to complete the final step in the imaging application.

Figure 12:
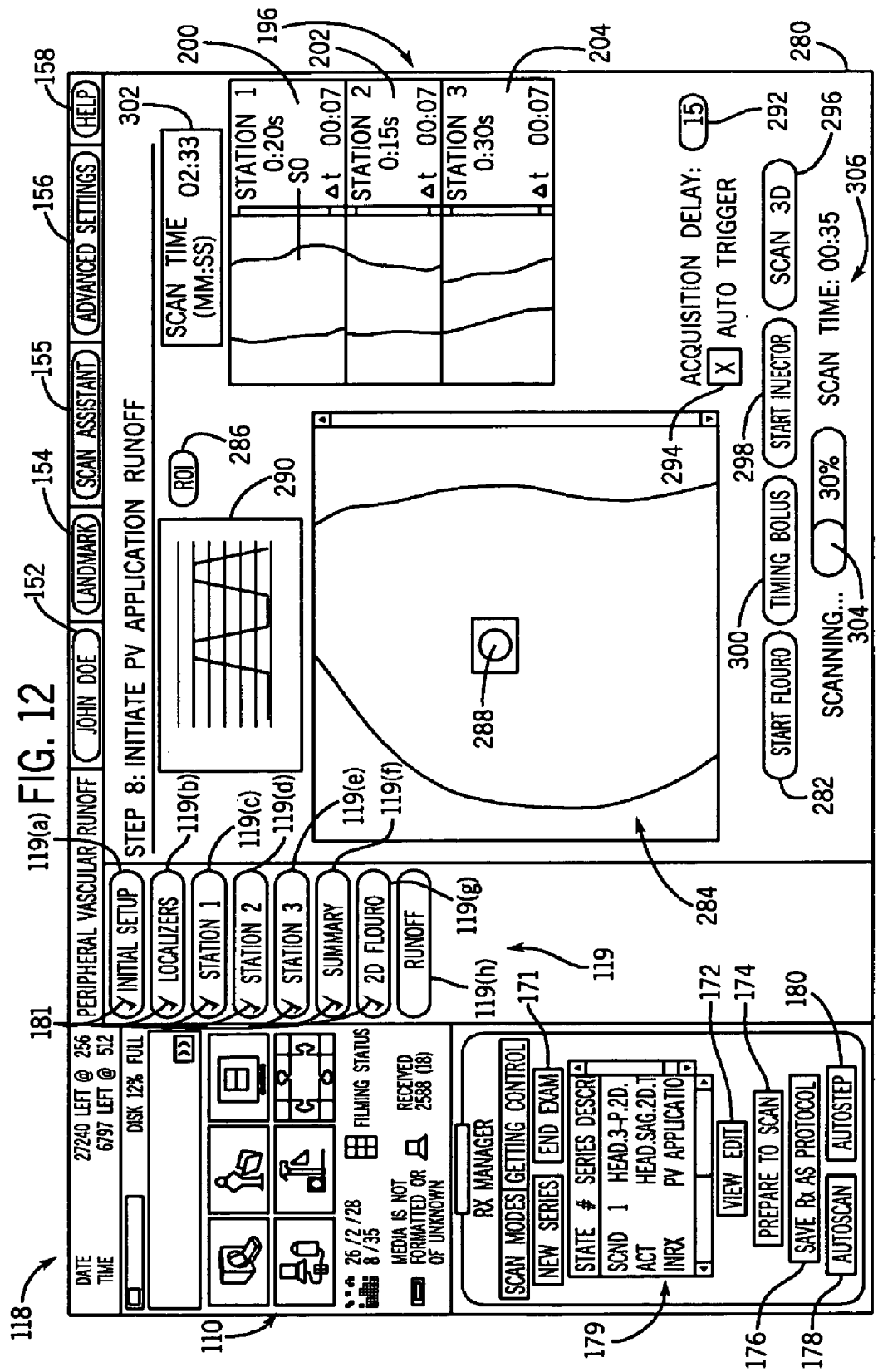
FIG. 12 is a representation of a graphical user interface for acquiring medical diagnostic image for the representative medical imaging application in accordance with the present invention.

Referring to FIG. 12, window 280 appears when tab 119(h) is selected. From window 280, the user can acquire arterial and venous images in one of two ways. First, the user may use a real-time fluoroscopy technique to acquire the images. To acquire the images the user will begin by pressing the "Start Flour" button 282, which will cause the viewer on this page to present the user with a real-time image 284 of the location that was prescribed and the "Start Fluoro" button will change its label to read "Pause Fluoro". At this point the user could do one, none or both of the following:

A. Select the "ROI" button 286 and draw a Region of Interest (ROI) 288 over the area of interest on the image in the viewer 284. This step is not required as the user could also visually detect bolus arrival. In this particular case, an ROI is used and as soon as it is placed on the image, the 290 in the top of window 280 updates with pixel intensity information.

B. Enter a time manually into the "Acquisition delay" text field 292. This can only be done if the "Auto Trigger" 294 is selected. In this case, the user leaves text field 292 at zero which tells the system that the user must manually press the "Go 3D" or "Scan" button 296 to initiate a scan.

After implementing the Fluoroscopy, the user may start the injector by pressing the "Start injector" button 298 which will essentially begin the injection of the contrast agent. If the "Acquisition Delay" 292 had a value greater than zero, the viewer would start a timer and would auto-scan when it reaches the same value displayed in the "Acquisition Delay" text field 292 if "Auto Trigger" 294 was selected. The user may watch the image 284 in the viewer as well as the graph 290 in order to detect the arrival of the contrast. Once the contrast is detected, it is time to begin the scan. The user may give any necessary instructions to the patient (i.e. hold breath) and press the "Scan" button 296, which will cause the sequence of arterial and venous image acquisitions to occur as prescribed in the "Summary" step. As these images are being acquired, they will be automatically displayed in the viewer. The user may scroll, pan/zoom, and window level these images.

A second way in which the user may acquire arterial and venous images is through the use of a timing bolus. To do this, the user must first prescribe the location for the fluoro image. The user may then start the fluoro acquisition by pressing the "Start Fluoro" button 282. As the fluoro acquisition is occurring in real-time, the user may prepare themselves and the patient and then press the "Timing Bolus" button 300. This will cause a few things to occur. First, button 300 will change to read "Mark Time" and still be active. Second, the image will display a timer 302 that is incrementing in seconds from the time the "Timing Bolus" button 300 is pressed and will not stop until the "Mark Time" button 300 is pressed. The final change from pressing the "Timing Bolus" button 300 is that the injector will inject a small amount of bolus into the patient, which the user will use to time the arrival of contrast into the fluoro image.

After the "Timing Bolus" button 300 is pressed, the user will watch the image 284, and possibly the graph 290, for the contrast to arrive. When the contrast is detected, the user presses the "Mark Time" button 300. This action will cause timer 302 on the image to stop incrementing. Further, a "Time to Start" text field (not shown) will become active with the same value as the timer on the image. Next, the user may decide to change the value of the "Time to Start" text field by simply highlighting the field and entering in a new value, or leave it as is. (Note: Throughout this process, the fluoro acquisition continues to occur.) Now the user may acquire the arterial and venous run images.

When "Start Injector" button 298 is pressed, the full amount of contrast agent is injected into the patient and the value in the text field and the timer on the image will begin counting down therefore functioning as a visual queue/ reminder to the user. If the auto trigger 294 is selected, the value in the text field and on the image reaches zero and scanner automatically begins acquiring the arterial and venous images. The user may manually press the "Go 3D" button 296 before the timer in the viewer reaches the value displayed in the "Time to Start" text field, but not after. If the auto trigger is not selected, the value in the text field and on the image only serves as a "guide" to the user that they should manually select the "Go 3D" button 296 when it reaches a value of zero. However, when the value does equal the "Time to Start" text field, nothing happens. Therefore, it is up to the user in this case to initiate the scan. They may do it before, after, or when the times equal. When the scan is initiated, a scanning timing bar 304 is displayed as well as a scan time timer 306.

After the user has completed the acquisition of the arterial and venous images the user may save this particular instance of the PV application as a protocol that may be implemented at a later date without reentering each parameter. This allows for buildup of a protocol database that may be accessed in the future. To save the protocol, the user selects the "Save Rx as Protocol" button 176 inside the Rx Manager 170 on left side of the GUI.

Figure 13:
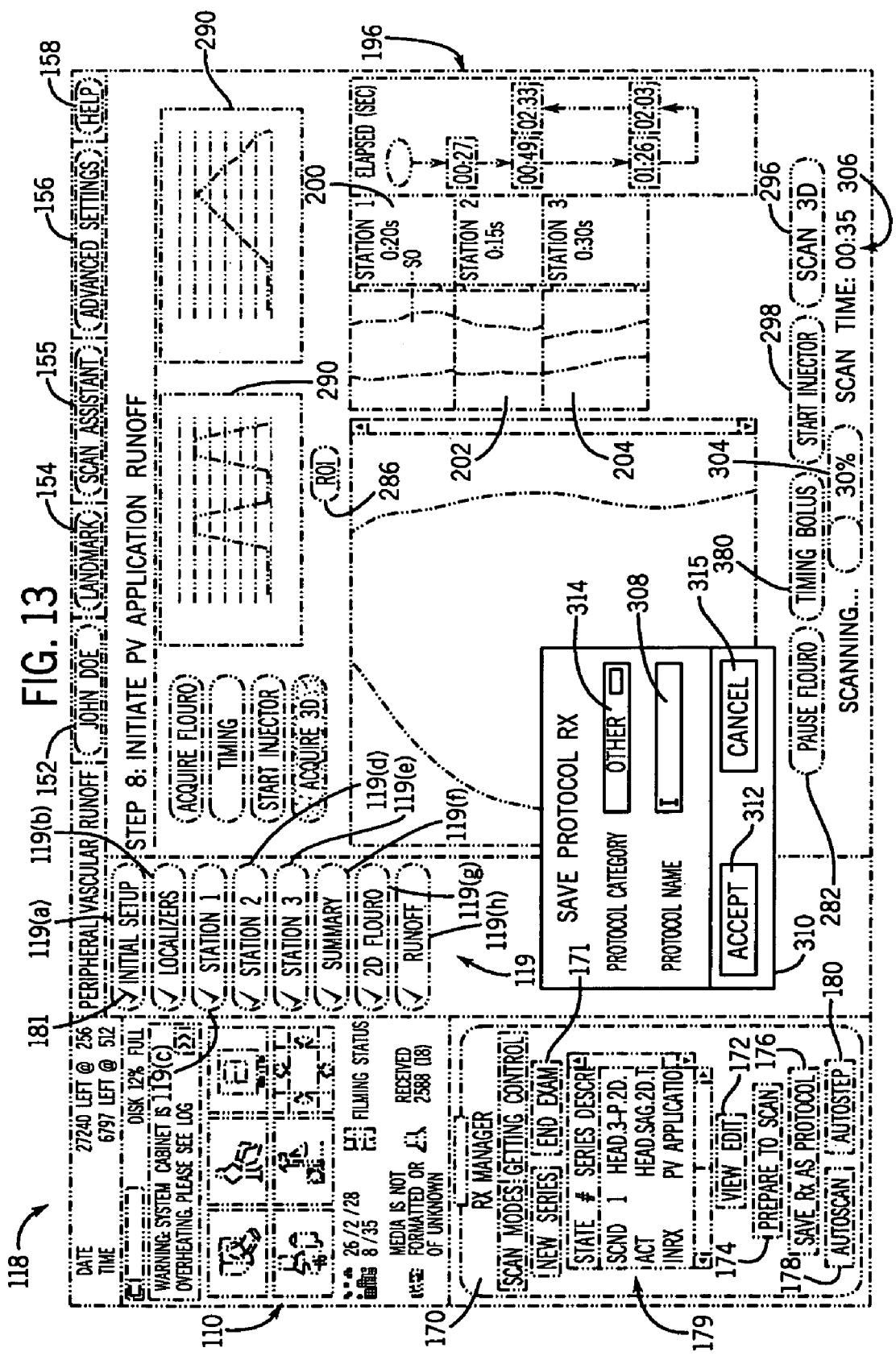
FIG. 13 is a representation of a pop-up dialog for use with the present invention.

Next and referring to FIG. 13, the user may enter the identifying name for this protocol in text field 308 of the "Save Protocol Rx" dialog 310 that pops up and select the "Accept" button 312. The user may also identify a protocol category using drill down menu 314. To cancel "saving" of the protocol the user may select button 315.

After this application is saved as a protocol, the user may want to close the exam as all series have been scanned. In order to end the exam, the user selects the "End Exam" button 171 on the left side of GUI 118. This will cause the current contents of the scan window to be closed.

Referring again to FIG. 4, the present invention allows for viewing and/or editing a screen series by selecting the "View Edit" button 172, or by double clicking a desired series 179. Either of these actions will cause the currently displayed window (immediately to the right of the Rx Manager) to be hidden, and the window associated with the selected series to be shown.

Figure 14:
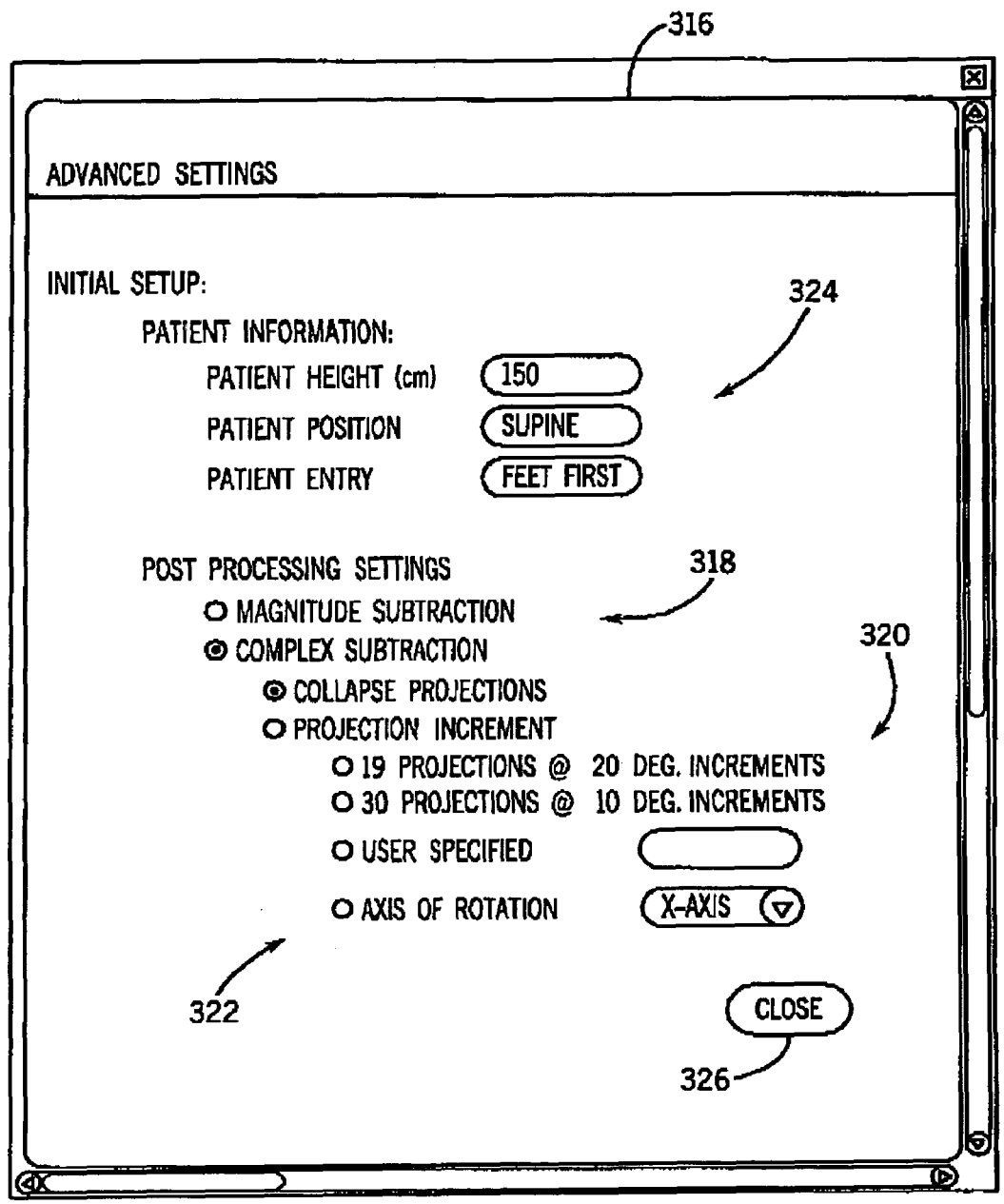
FIG. 14 is a representation of a graphical user interface for setting up advanced scan settings for the representative medical imaging application in accordance with the present invention.

Referring to FIG. 14, the present invention includes an "Advanced Settings" window 316 which allows the user access to all parameters, features, and tools associated with a particular application for viewing and/or editing. For example, window 316 allows the user to access parameters associated with image subtraction 318, image projections 320, as well as all scan and application parameters 322 that are not presented to the user throughout the steps of the application. The user may also view/edit advanced settings regarding patient information 324.

Additionally, when the user launches the "Advanced Settings" window, the presentation within the dialog window will contain the parameters and advanced settings for the currently selected step in the application. This will be referred to as "context sensitive" behavior. For example, if the user has the "Initial Setup" window selected when the "Advanced Settings" button is clicked, the window that displays will be set to the parameters and advanced settings for the initial setup. Also, this dialog will contain the parameters and advanced settings for all components of the application, which can be reached via the scroll bar on the right-hand side of the dialog window. Note that the parameters and advanced settings are organized and listed in the dialog window in the same order that they appear in the application (i.e. "Initial Setup", "Localizers", . . . , "Run-Off"). Once the user completes viewing/editing, window 316 may be closed by selecting button 326.

Figure 15:
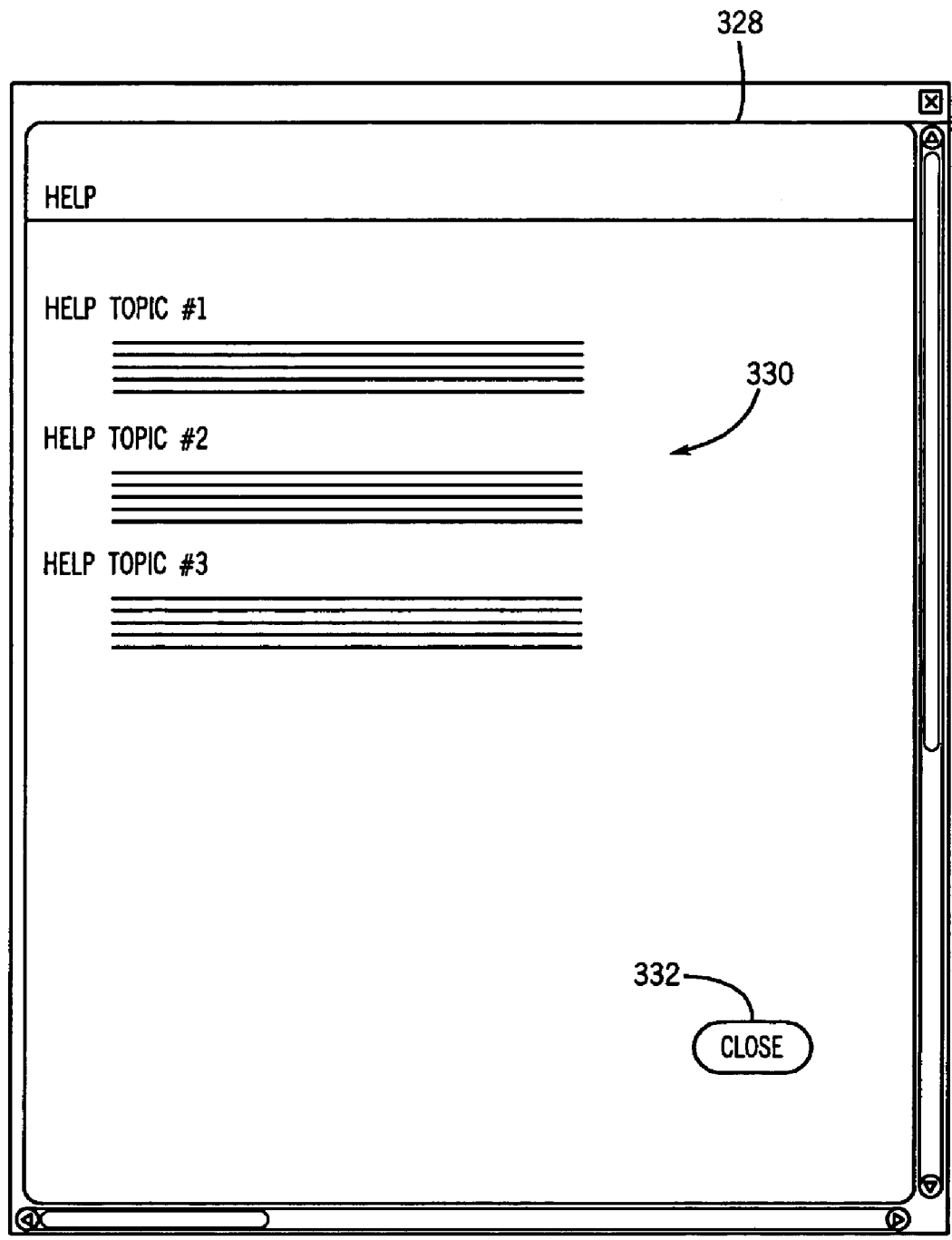
FIG. 15 is a representation of a graphical user interface for displaying help topics for the representative medical imaging application in accordance with the present invention.

Referring to FIG. 15, a "Help" window 328 appears upon selection of "Help" button 158, FIG. 4. A number of help topics 330 may be listed to help the user clarify any issue. The help topics 330 may be application specific or specific to the activities of a particular tab 119(a–h).

Much like the "Advanced Settings" window, FIG. 13, the "Help" dialog is context sensitive. So, in this case when the dialog comes up the first choices presented to the user should relate directly to the currently selected step. Therefore, if the "Initial Setup" step was selected, the options in the "Help" window 328 should include projection and collapse images amongst other topics. Also, window 328 will allow the searching of all topics contained in the help system. The purpose of the help system, will be to answer user questions regarding how to complete an application, medical imaging physics questions, and serve as a place holder for user notes about a particular topic or application. The user may select close button 332 to close window 328.

Figure 16:
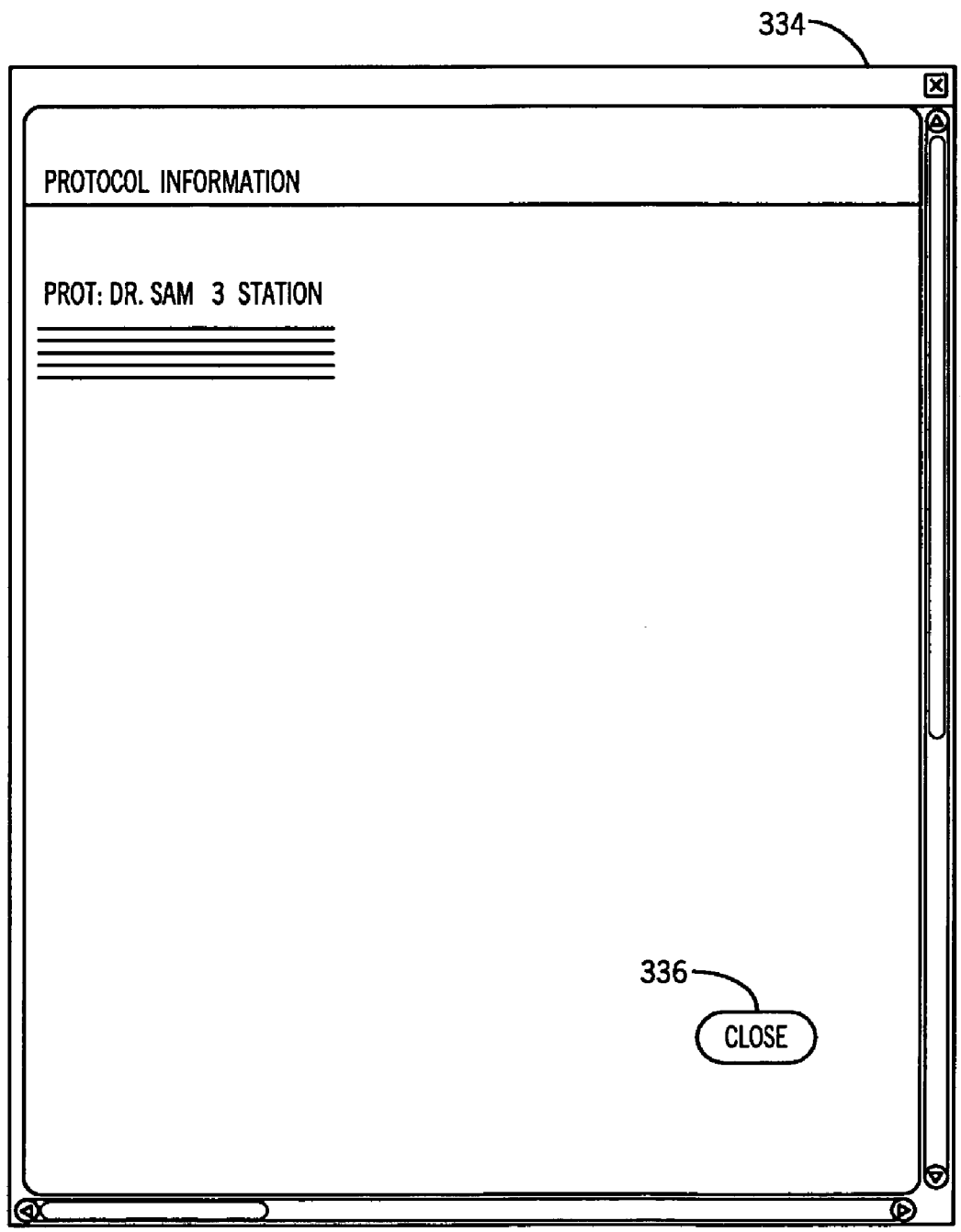
FIG. 16 is a representation of a graphical user interface for displaying protocol information for the representative medical imaging application in accordance with the present invention.

Referring to FIG. 16, a protocol window 334 may be viewed which displays the contents that are not "context sensitive". That is, the protocol information window 334 will always contain the same options for each application. All that will change between instances of the application are the values and settings for these options. Also, in one embodiment, these options can only be viewed in window 334 as they are not editable. After viewing the protocol information, the user may close window 334 by selecting close button 336.

As discussed above, the present invention includes an "Advanced Settings" window whose context is adaptive to display those parameters and settings associated with a particular tab. These settings allow access to all possible application parameters and features for users that have special needs. For example, the "Localizer" tab in the PV application only displays a few scan parameters for each station. These options have been determined to be the most important, but some users may want access to other options. If so, the user need only select the "Advanced Settings" button and a page will be presented with all available options and features of the specific imaging application. The information that will be displayed to the user when the "Advanced Settings" button is pressed will depend on the currently selected step in the application. Like the "Help" window, the "Advanced Settings" window will be context sensitive in that it will display the parameters and advanced settings for the particular step in the application that is selected when the "Advanced Settings" is pressed. However, the user can still access any of the other parameters and advanced settings available for other steps in the application. The Advanced Settings for each modularizing tab are set forth below:1.
  Initial Setup:
  Patient Height
  Patient Position
  Patient Entry
  Magnitude Subtraction
  Complex Subtraction
  Collapse Projections
  Projection Increment
  19 projections @ 20 deg. Increments
  38 projections @ 10 deg. Increments
  User Specified
  Axis of Rotation
  2.Localizers:
  FOV Slice Thickness
Spacing
Frequency
Phase
NEX
Phase FOV
Auto Center Frequency
Autoshim
Contrast
Coverage; center of FOV (R/L, A/P, S/I)
Number of slices per plane
Scan controls (scan, prescan, manual prescan, auto prescan)
Different number of images per 3-plane
3.3D Rx:
Plane
Mode
TE
Flip Angle
Bandwidth
FOV
Slice Thickness
Locs per slab/no. of slices
Frequency
Phase
NEX
Phase FOV
Frequency direction
Auto center frequency
no. of slabs
It uses the following options:
Variable bandwidth
ZIP2
ZIP512
CV10→ Special (on/off)
CV12→ Elliptic Centric (on/off)
Referse elliptic centric
4.Summary:
None
5.Fluoro Rx:
Plane
Mode
TE/TI
Tr
Flip Angle
Bandwidth
FOV
Slice Thickness
Matrix Frequency
Matrix Phase/PFOV
NEX
Frequency Direction
Auto Center Frequency As indicated previously, the present invention utilizes a "Humanoid" configured to function as a visual tool that allows the user to interact with and navigate the application, gather data about the exam, and view images. The "Humanoid" displays localizer images for each station and allows access to a station's GRx viewer by "double-clicking" on the corresponding image. Further, the images will display prescription overlap from one view image to the another. "Double-clicking" an image in the "Humanoid" will immediately take the user to the step corresponding to that station's GRx. For example, selecting the middle viewer on the "Humanoid" will cause the current window to change to the window that would appear as if the "Station 2" tab had been selected. The station label will change slightly when the user is prescribing that station to indicate to which is the active station. The scan times displayed on the "Humanoid" will be updated dynamically based on changes. A user can scroll through the selected images in a viewer. A user can window/level the selected images in a viewer. A user can select and view different localizer planes on the "Humanoid" as well.

The present invention allows for messages to be displayed to a user. The error messages may be separated into two categories: application level messages and system/safety messages. System and safety level messages may be displayed in the upper left hand side of the GUI 118, FIG. 4. There are a couple of ways in which application level messages will be presented to the user. First, text messages may be placed within the applications panel underneath the tabbed pane and above the "Scan Ops" area of the screen. Another way in which these messages may be presented is through pop-up displays to the user. In the former case, the messages will typically be informational. The messages in the latter case will be due to erroneous user input into scan parameter fields.

In a further embodiment, the present invention includes a series of graphical windows that for the purposes of this application will be collectively referred to as a "Scan Assistant". In known systems, the mechanism for preventing erroneous input of scan parameters by a user is to present to the user change in scan parameter label colors indicates a specific scan parameter value is out of range and needs to be changed to a suggested value. While the user is shown a valid range of the value read scan parameter, these systems fail to provide any information to indicate that scan parameters are inter-related and can depend on one another. If the value of one scan parameter is changed, it most probably affects another parameter value but with these known systems the user is not made explicitly aware that such a change has occurred unless the change causes a value to go outside a valid min/max range of values.

During a typical prescription of a scan session, a user wants to accomplish a number of tasks, such as, reducing scan time, increasing resolution, increasing contrast, and increasing signal-to-noise ratio. Other common tasks the user may wish to accomplish during the scan prescription include increasing coverage (i.e. number of slices), entering values outside a current valid range, and providing guidance on scan parameter dependencies. Current systems are capable of assisting the user in accomplishing each of these tasks, but not easily. Further, the user must fully understand at a physics level the inter-dependencies between scan parameters and manually change these parameters in a way that accomplishes the intended result.

The present invention solves these drawbacks by demonstrating the relationship between scan parameters, notifying the user of scan parameter validity, as well as suggesting possible ways to achieve a pre-defined set of specific goals, such as reducing scan time, increasing resolution, increasing contrast, increasing signal-to-noise ration, and increasing coverage.

The present invention provides prescription guidance by notifying the user when the user changes a scan parameter value of those other scan parameters that have been automatically changed, are out of a valid range, and require the user to enter a new value. That is, if the user inputs a scan parameter value that causes another scan parameter value to be changed and the change to the other scan parameter is valid, the scan assistant will notify the user that the other scan parameter value is valid and has therefore been automatically changed. However, if the user changes a scan parameter value which causes another scan parameter to be out of the valid range, the scan assistant will notify the user that the other scan parameter is now out of a valid range and is therefore invalid. Further, if the user changes a scan parameter value, the scan assistant is also configured to notify and prompt the user to enter a new scan parameter value for another scan parameter value that is dependent upon the changed parameter value.

The present invention further provides prescription guidance by prioritizing all the scan parameters into three categories on a per scan session or experiment basis. The scan parameters are prioritized into a primary, secondary, and tertiary group. This ranking defines the relationship between parameters and provides guidance how their values may be affected based on user input. For example, change in the value of a primary parameter, such as FOV, may affect other primary parameters as well as secondary parameters, such as, resolution, and tertiary parameters, such as, timing. However, changing a secondary parameter value may affect other secondary parameters as well as tertiary parameters, but would not affect a primary parameter. Moreover, changing a tertiary parameter may only affect other tertiary parameter values. This ranking promotes the notion of driving the physics from the geometry to the timing, rather than from timing to geometry as is typically done in known systems. Because the scan assistant recognizes the parameter relationship, it may assist the user in achieving the desired timing by facilitating geometry trade-offs.

Referring to FIGS. 17–21, the Scan Assistant facilitates prescribing a scan session with reduced scan time, increased resolution, increased contrast, increased signal-to-noise ratio, and increased coverage by presenting the user with these options in a series of graphical windows. The user need only select the specific task option and the Scan Assistant will then display a list of possible ways to achieve the intended result as well as displaying trade-offs associated with achieving the intended result at the expense of other limitations of the system. The displayed trade-offs or consequences may be dynamically determined based on user input or, alternatively, include a list of canned or common trade-offs associated with modifying the particular trade option.

Figure 17:
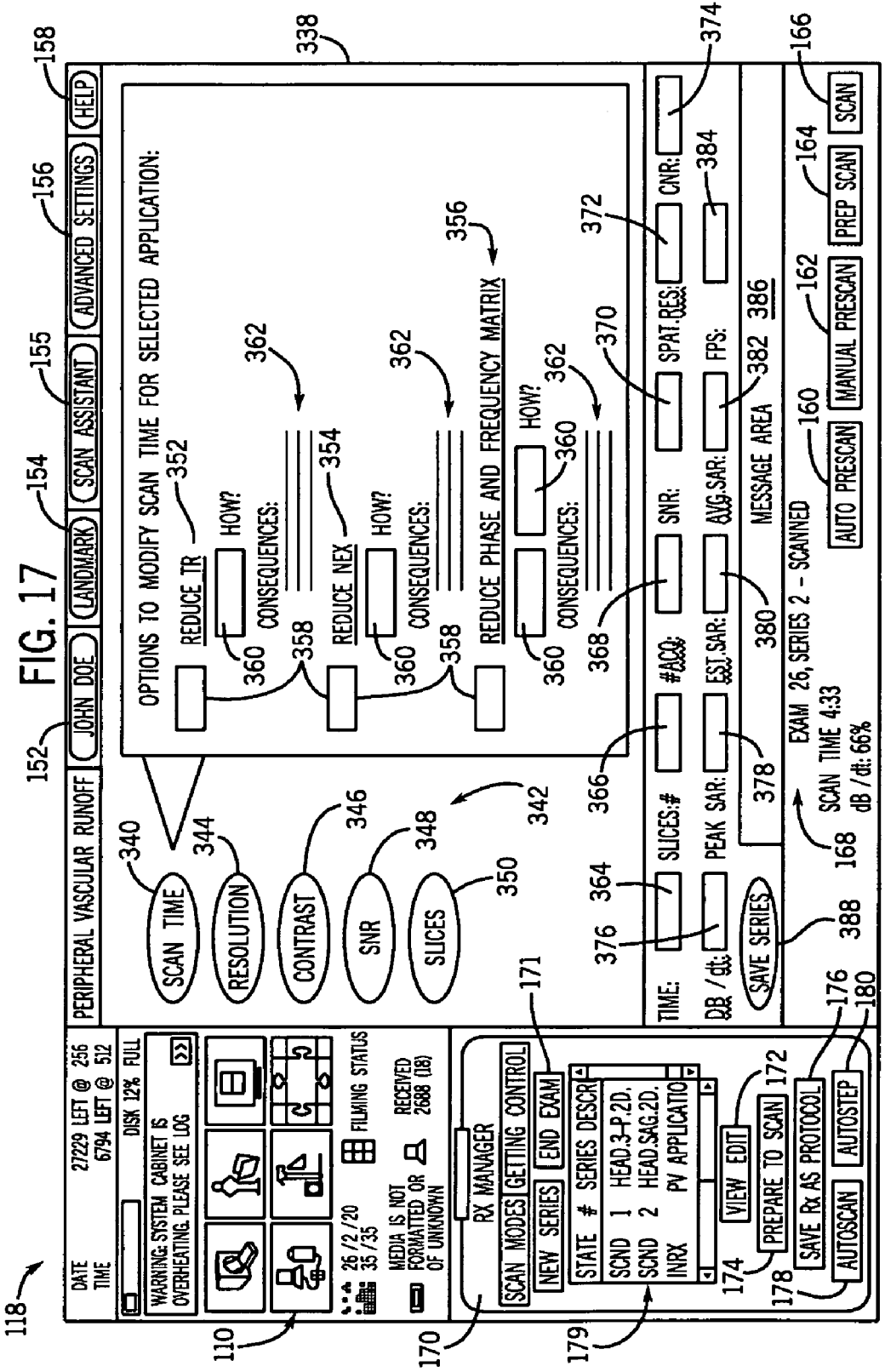
FIG. 17 is a representation of a graphical user interface for modifying scan time in accordance for the representative medical imaging application with the present invention.

Now referring to FIG. 17, window 338 is displayed on GUI 118 when the user selects "Scan Assistant" button 155 followed by a selection of "Scan Time" tab 340. "Scan Time" tab 340 is one of a number of tabs 342 that allows the user to complete a fixed set of tasks related to prescribing a scan session or scan experiment. The additional buttons include a "Resolution" tab 344, a "Contrast" tab 346, an "SNR" tab 348, and a "Slices" tab 350. As indicated previously, window 338 is displayed when tab 340 is selected. Window 338 displays a number of options that may be modified for the selected application that are associated with scan time. For example, the user may select reduce TR 352, reduce NEX 354, or select reduce phase-in-frequency matrix 356 to further modify scan time for the selected application. Each option further includes a checkbox 358 that the user may select to indicate to the system that an option is to be edited. The user may then input modified scan values in field 360 for each selected option. When the user inputs a scan parameter value for any option in field 360, a number of the most common consequences associated with changing that parameter value appear in field 362. This allows the user to determine, in real-time, the effects of changing a particular scan parameter value.

Window 338 further includes a number of scan parameter display fields to convey general scan parameter data to the user. These additional scan parameter values include time 364, number of slices 366, number of acquisitions 368, SNR 370, spatial resolution 372, CNR 374, DB/DT 376, Peak SAR 378, estimated SAR 380, average SAR 382, and FPS 384. A message area 386 is also provided to be used to convey messages to the user. A "Saved Series" tab 388 may be used to save modified scan parameter values.

Figure 18:
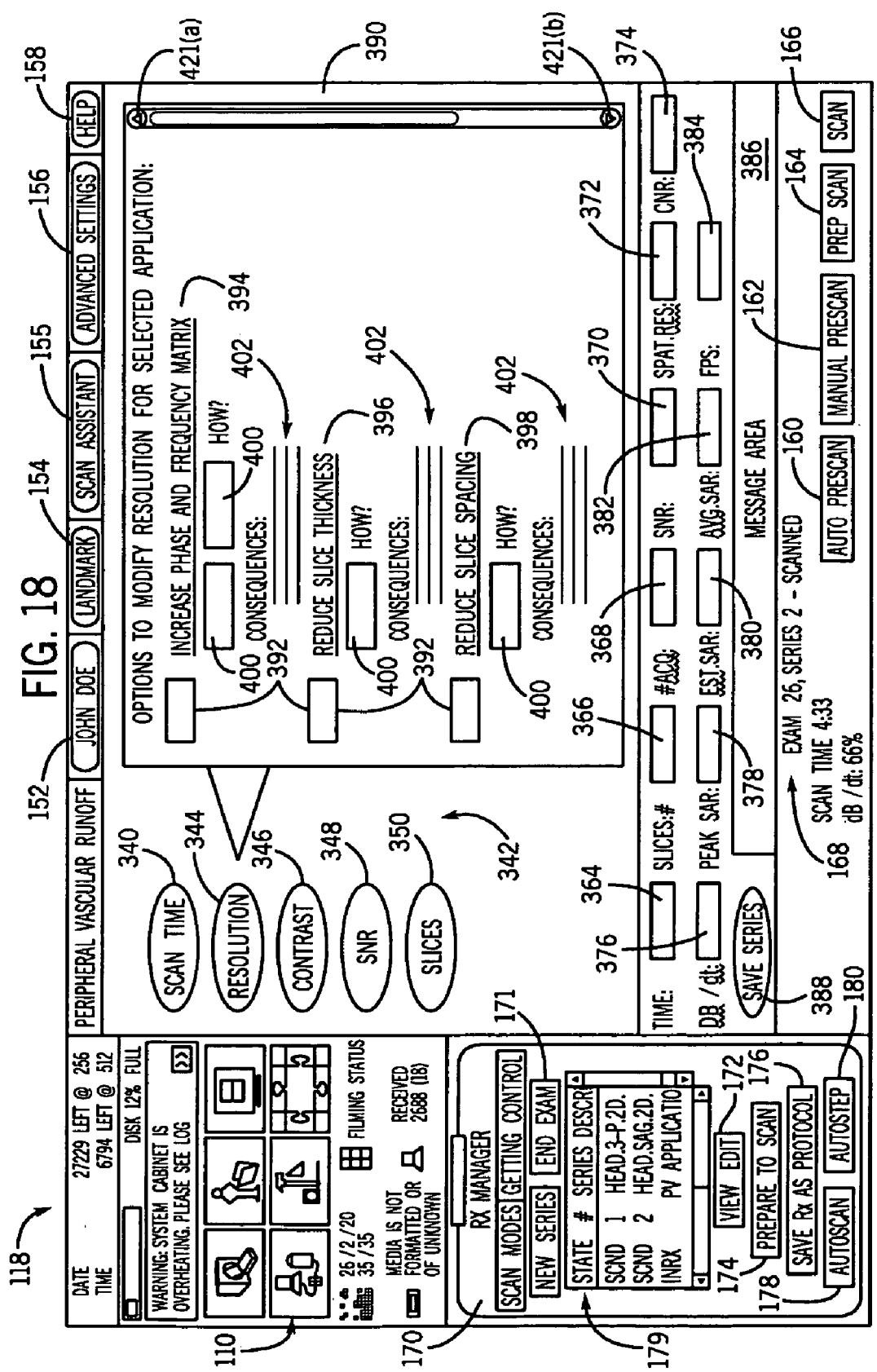
FIG. 18 is a representation of a graphical user interface for modifying the resolution for the representative medical imaging application in accordance with the present invention.

Referring to FIG. 18, when the user selects "Resolution" tab 344 window 390 is displayed that allows the user to modify the scan parameter values associated with resolution. Similar to window 338 of FIG. 17, window 390 includes a number of boxes 392 that may be selected to indicate to the system that a particular scan parameter is to be modified. In the embodiment shown in FIG. 18, the options which may be modified for the selected application related to the resolution functions include increase phase in frequency matrix 394, reduce slice thickness 396, reduce slice spacing 398, and reduce FOV (not shown). The user may input a new scan parameter value or modify an existing scan parameter for each option by entering data in fields 400 corresponding to each particular option. Inputting of a modified scan parameter value will again result in a number of consequences associated with modifying the scan parameter value to appear on window 390 in fields 402.

Figure 19:
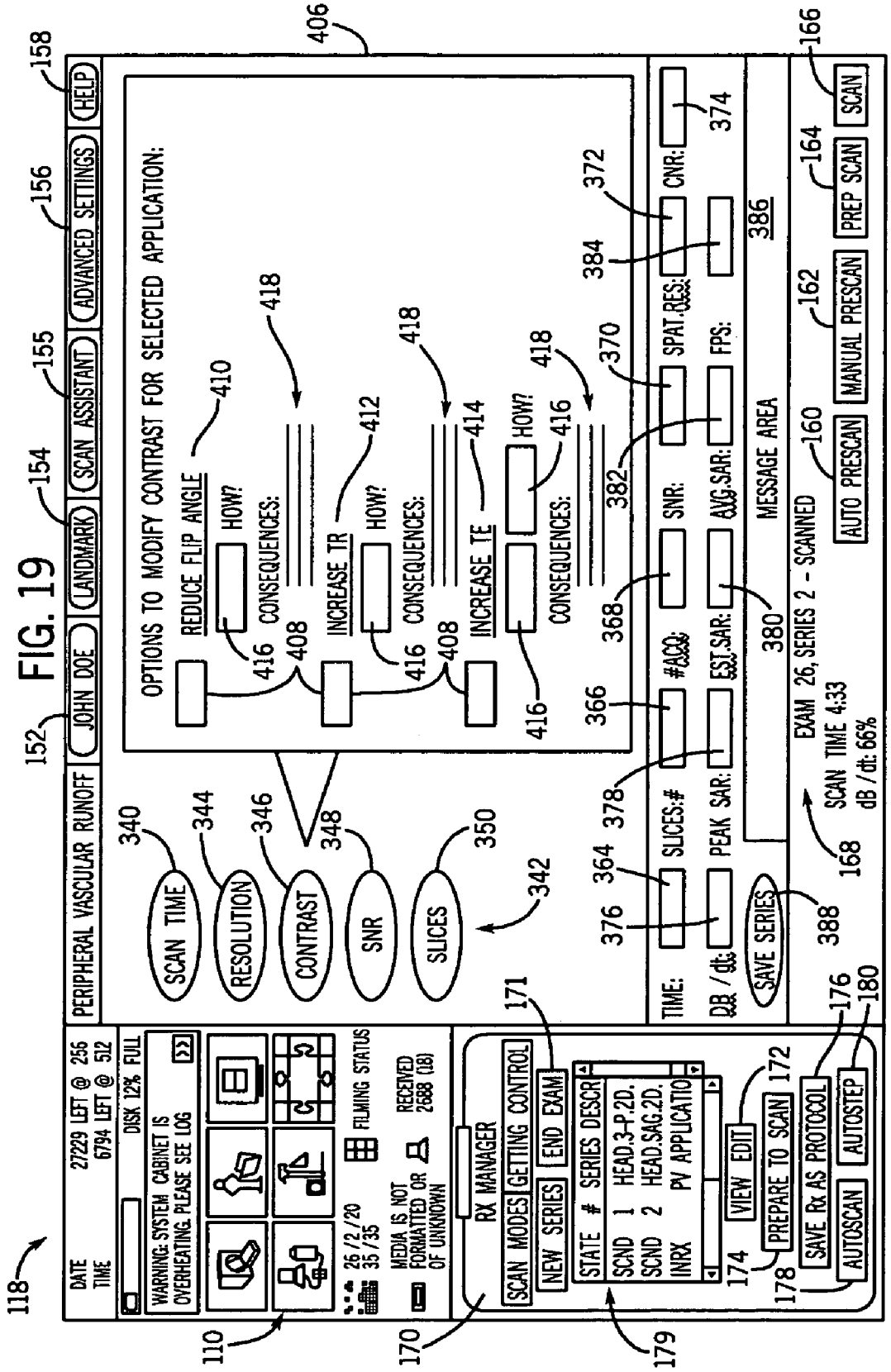
FIG. 19 is a representation of a graphical user interface for modifying the contrast for the representative medical imaging application in accordance with the present invention.

Referring to FIG. 19, selection of "Contrast" tab 346 will result in window 406 being displayed. Window 406 allows the user to modify options related to the contrast for the selected application. Boxes 408 are provided that may be "checked" to indicate that a particular option is to be modified. In this embodiment, the options include reduce flip angle 410, increase TR 412, and increase TE 414. The user may input modified data for each selected option in a corresponding field 416. When the user inputs the modified scan parameter value in field 416, the system automatically determines and displays a number of consequences associated with modifying the scan parameter value in field 418.

Figure 20:
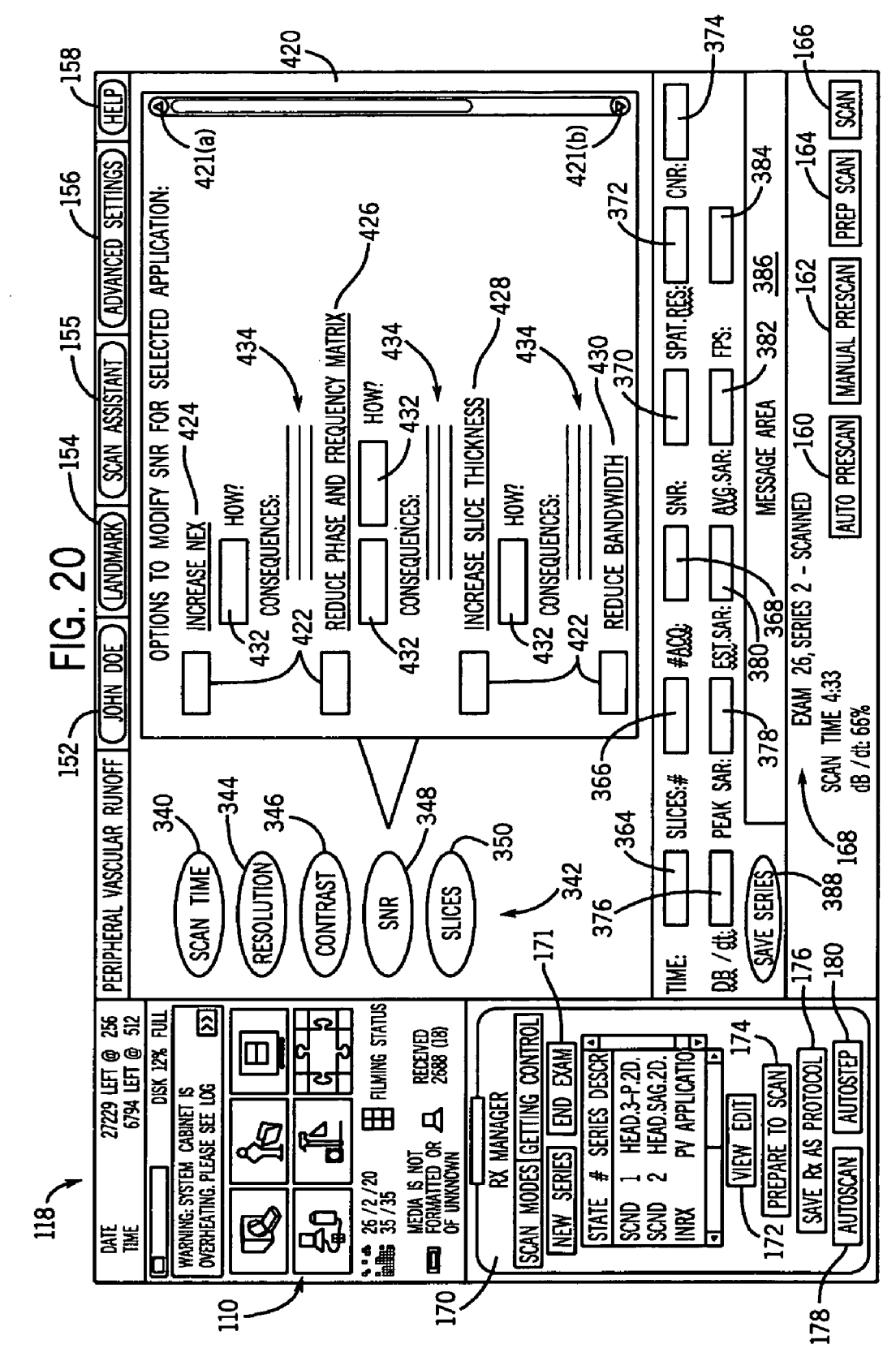

Now referring to FIG. 20, window 420 is displayed when the user selects "SNR" tab 348. Selection of "SNR" tab allows the user to modify options for the particular application related to signal-to-noise ratio. The user may indicate that a particular option is to be modified by marking box 422 corresponding to each available option. In this embodiment, the available options include increase NEX 424, reduce phase and frequency matrix 426, increase slice thickness 428, and reduce bandwidth 430. After selecting a particular option to be modified, the user may input modified scan parameter value for particular option in fields 432 which results in the system automatically determining and displaying in field 434 the consequences associated with modifying the SNR value to the value input by the user. The user may scroll window 420 using tabs 421(a) and 421(b).

Now referring to FIG. 21, selection of "Slices" tab 350 results in window 436 being displayed to the user. Window 436 allows the user to modify options related to coverage for the selected application. The user may do so by first selecting box 438 corresponding to a particular option to be modified. In this embodiment, the modifiable options include increase TR 440, reduce TE 442, increase bandwidth 444, and reduce frequency matrix 446. After selecting an option to modify, the user may input modified scan parameter values in a corresponding field 448 for each selected option. The system will then automatically determine based on the hierarchical nature of the scan parameter values, as discussed previously, display the consequences 450 of modifying the scan parameter value as input by the user.

In another preferred embodiment, the system automatically detects modification of a parameter rather than relying on a user to first select a "check box" signaling to the system that an option is to be modified.

Once the user has modified each option desired, the user may save the modified parameters for the particular application by depressing "Save Series" tab 388. It should be noted, that the user need not view each window to save the series. That is, the user may elect to modify the options associated with scan time and contrast by viewing only those windows associated with those tabs but may elect not to modify the remaining tasks associated with a particular application. The user need not display each of the other tabs to save the series.

The present invention has been described with particular reference to a PV application implemented with an MR imaging system. However, the teachings of the present invention related to logical guidance of workflow for acquiring imaging data on a single GUI may be applicable to other medical imaging systems such as, CT, PET, X-ray, and ultra-sound.

Therefore, in accordance with one embodiment of the present invention, a graphical user interface is provided for prescribing a medical imaging session, acquiring diagnostic images, and processing imaging data. The GUI comprises a plurality of modularizing selectors configured to facilitate workflow through a medical imaging application. A plurality of status indicators are also provided wherein each status indicator corresponds with a modularizing selector and configured to display at least one of selection of the modularizing selector and completion of tasks associated with the modularizing selector. The GUI further includes a messaging module configured to automatically display messages regarding the MR application.

In accordance with another embodiment of the present invention, a graphical workflow management tool is provided for prescribing a medical imaging scan. The tool includes a GUI configured to be visually displayed on a console of a medical imaging system. The tool further includes a plurality of prescription tabs aligned vertically on the GUI. A plurality of status indicators are also provided on the GUI wherein each indicator is configured to display a status of activities for a corresponding prescription step. The tool further includes a plurality of context-specific tabs aligned horizontally on the GUI.

In yet another embodiment of the present invention, an MR apparatus includes a computer programmed to receive a launch MR application command and launch the MR application in response thereto. The computer is further programmed to receive a number of application steps. The computer is further programmed to display a GUI on a console, the GUI having a number of tabs equal to the number of identified application steps. The computer is also programmed to initialize a localizer scan for at least one localizer application step and display status of the localizer scan on the GUI and receive a prescription command and acquire MR images in response to the received prescription command for an application step. The computer is also programmed to receive another prescription command and acquire MR images in response to the received prescription command for another application step. Alternatively, the computer may be programmed to conduct prescription workflow for a number of identified sub-applications.

In a further embodiment of the present invention, a method of acquiring diagnostic images is provided and includes receiving a launch application instruction and launching the application. The method further includes determining a number of stations based on a received user input, wherein each station includes a number of localizers. The method also includes acquiring imaging data and displaying the imaging data on a GUI, the GUI having a number of context-specific tabs and a number of modularizing tabs.

The present invention has been described in terms of the preferred embodiment, and it is recognized that equivalents, alternatives, and modifications, aside from those expressly stated, are possible and within the scope of the appending claims.

The invention claimed is:

1. A GUI for prescribing medical imaging sessions comprising:
    a plurality of modularizing selectors configured to facilitate workflow through an imaging application;
    a plurality of status indicators, each status indicator correlating with a modularizing selector and configured to display at least one of selection of the modularizing selector and completion of tasks associated with the modularizing selector; and
    a dedicated messaging module configured to be persistently displayed across variations in the plurality of modularizing selectors and the plurality of status indicators and to automatically display messages regarding the imaging application.

2. The GUI of claim 1 further comprising at least two application regions and wherein the plurality of modularizing selectors are aligned vertically in a single application region.

3. The GUI of claim 2 further comprising a plurality of windows corresponding in number to the plurality of modularizing selectors, the plurality of windows configured to present a number of scan parameters.

4. The GUI of claim 1 further comprising at least one of a scan status indicator and a list of components necessary to initiate scan activity.

5. The GUI of claim 4 further comprising a messaging region and wherein the messaging module and the at least one of the scan status indicator and the list of components are displayed in the messaging region, and wherein the messaging region is positioned in a lower portion of the GUI.

6. The GUI of claim 1 wherein the messaging module includes a pop-up dialog configured to display an invalidity of a user input.

7. The GUI of claim 1 further comprising a plurality of application-specific selectors that upon user selection each application-specific selection is configured to display a window specific to the imaging application and wherein the plurality of application-specific selectors are horizontally oriented.

8. The GUI of claim 7 wherein the plurality of application-specific selectors include a landmark selector, a patient information selector, an advanced settings selector, and a help selector, and wherein each of application-specific selector is configured to launch a application specific window upon user selection, wherein the application specific windows include a landmark window configured to aid user positioning of a scan subject, a patient information window configured to display patient information, an advanced settings and parameters window configured to display advanced settings and parameters for the imaging application, and a help configured to display assistance information related to the imaging application.

9. The GUI of claim 1 having a Layout configured to facilitate left-to-right and top-to-bottom MR prescription workflow to guide a user logically through a managed prescription.

10. An MRI apparatus to prescribe an imaging session and acquire imaging data, the MRI apparatus comprising:
- a magnetic resonance imaging (MRI) system having a plurality or gradient coils positioned about a bore of a magnet to impress a polarizing magnetic field, and an RF transceiver system and an RF switch controlled by a pulse module to transmit RF signals to an RF coil assembly to acquire MR images;
- a computer programmed to:
- (A) receive a launch MR application command;
- (B) launch an MR application;
- (C) receive a number of application step identifiers;
- (D) display a GUI on a console, the GUI having a number of tabs equal to the number of identified application steps;
- (E) initiate a localizer scan for at least one localizer and display a status of the localizer scan on the GUI;
- (F) receive a prescription command and acquire MR images in response to the received prescription command for an application step; and
- (G) receive another prescription command and acquire MR images in response to the received another prescription command for another application step.

11. The MR apparatus of claim 10 wherein the computer is further programmed to repeat (G) for a remaining application step.

12. The MR apparatus of claim 10 wherein the computer is further programmed to display, on the GUI, the acquired MR images.

13. The MR apparatus of claim 10 wherein the computer is further programmed to receive a re-prescription command for an application step and reacquire previously acquired MR images for the application step.

14. The MR apparatus of claim 10 wherein the computer is further programmed to display a series of prescription windows on the GUI.

15. The MR apparatus of claim 10 wherein the computer is further programmed to reposition an MR image on the GUI in response to a imaging reposition user input.

16. The MR apparatus of claim 10 wherein the computer is further programmed to continually display a scan status on the GUI, wherein the scan status includes one of stand-by, in-progress, and completed.

17. The MR apparatus of claim 10 wherein the number of tabs are positioned vertically on the GUI, the GUI including a number of context-specific selectors positioned horizontally along a top region thereof.

18. The MR apparatus of claim 10 wherein the computer is further programmed to display a summary module on the GUI, the summary module enabling review of prescription commands for acquiring medical imaging data.

19. A method for acquiring medical images comprising:
- receiving a launch application instruction;
- launching the application;
- determining a number of prescription steps based on a received user input;
- displaying a GUI for prescribing an imaging session, the GUI having a number of vertically aligned modularizing tabs corresponding to the number of prescription steps;
- wherein the GUI includes a number of context-specific tabs horizontally aligned;
- wherein the numbers of modularizing tabs are configured to facilitate a logical and structured workflow of prescribing a medical imaging session; and
- displaying a number of status indicators on the GUI, the number of status indicators configured to indicate completion of a prescription step.

20. The method of claim 19 wherein the number of context-specific tabs are arranged horizontally across a top region of the GUI.

21. The method of claim 19 wherein the number of modularizing tabs are arranged vertically along a generally left region of the GUI.

22. The method of claim 19 further comprising displaying messages to an operator in a bottom region of the GUI.

23. The method of claim 22 wherein the messages include at least one of scanner information, user messages, state of current application, scan times, availability of another scan, status of other scan applications, and a list of components necessary to initiate scan activity.

* * * * *

UNITED STATES PATENT AND TRADEMARK OFFICE
CERTIFICATE OF CORRECTION

| | | |
|---|---|---|
| PATENT NO. | : 7,020,844 B2 | |
| APPLICATION NO. | : 09/683129 | |
| DATED | : March 28, 2006 | |
| INVENTOR(S) | : Trevino et al. | |

It is certified that error appears in the above-identified patent and that said Letters Patent is hereby corrected as shown below:

Col. 20, line 64 (Claim 9), delete "Layout" and substitute therefore -- layout - -;

Col. 21, line 4 (Claim 10), delete "or" and substitute therefore -- of --;

Col. 22, line 21 (Claim 19), delete "numbers" and substitute therefore -- number --.

Signed and Sealed this

Fifteenth Day of August, 2006

JON W. DUDAS
*Director of the United States Patent and Trademark Office*